US008008348B2

(12) United States Patent (10) Patent No.: US 8,008,348 B2
Steiner et al. (45) Date of Patent: *Aug. 30, 2011

(54) TREATING MUSCLE WASTING WITH SELECTIVE ANDROGEN RECEPTOR MODULATORS

(75) Inventors: Mitchell S. Steiner, Germantown, TN (US); Karen A. Veverka, Cordova, TN (US); James T. Dalton, Upper Arlington, OH (US); Duane D. Miller, Germantown, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 2177 days.
This patent is subject to a terminal disclaimer.

(21) Appl. No.: 10/861,923

(22) Filed: Jun. 7, 2004

(65) Prior Publication Data
US 2010/0144871 A1 Jun. 10, 2010

Related U.S. Application Data

(63) Continuation-in-part of application No. 10/310,150, filed on Dec. 5, 2002, now Pat. No. 7,547,728.

(60) Provisional application No. 60/336,185, filed on Dec. 6, 2001.

(51) Int. Cl.
*A61K 31/275* (2006.01)
*A61K 31/32* (2006.01)
*A61K 31/16* (2006.01)
*A61K 31/165* (2006.01)

(52) U.S. Cl. ........ 514/522; 514/524; 514/493; 514/616; 514/619

(58) Field of Classification Search .................. 514/522, 514/524, 493, 616, 619
See application file for complete search history.

(56) References Cited

U.S. PATENT DOCUMENTS

| | | |
|---|---|---|
| 3,875,229 A | 4/1975 | Gold |
| 4,139,638 A | 2/1979 | Neri et al. |
| 4,191,775 A | 3/1980 | Glen |
| 4,239,776 A | 12/1980 | Glen et al. |
| 4,282,218 A | 8/1981 | Glen et al. |
| 4,386,080 A | 5/1983 | Crossley et al. |
| 4,465,507 A | 8/1984 | Konno et al. |
| 4,636,505 A | 1/1987 | Tucker |
| 4,880,839 A | 11/1989 | Tucker |
| 5,162,504 A | 11/1992 | Horoszewicz |
| 5,609,849 A | 3/1997 | Kung |
| 5,656,651 A | 8/1997 | Sovak et al. |
| 6,019,957 A | 2/2000 | Miller et al. |
| 6,071,957 A | 6/2000 | Miller et al. |
| 6,160,011 A | 12/2000 | Miller et al. |
| 6,482,861 B2 | 11/2002 | Miller et al. |
| 6,492,554 B2 | 12/2002 | Dalton et al. |
| 6,569,896 B2 | 5/2003 | Dalton et al. |
| 6,995,284 B2 | 2/2006 | Dalton et al. |
| 7,547,728 B2 * | 6/2009 | Steiner et al. ............... 514/522 |
| 2001/0012839 A1 | 8/2001 | Miller et al. |

FOREIGN PATENT DOCUMENTS

| | | |
|---|---|---|
| EP | 0 040 932 | 2/1981 |
| EP | 0 100 172 | 2/1984 |
| EP | 000 2892 | 2/1985 |
| EP | 00198352 | 1/1989 |
| EP | 0253 503 | 12/1991 |
| GB | 1360001 | 3/1970 |
| JP | 52-128329 | 10/1977 |
| JP | 54-63047 | 12/1980 |
| WO | WO 95/19770 | 7/1995 |
| WO | WO 98 05962 | 2/1998 |
| WO | WO 98/53826 | 12/1998 |
| WO | WO 98/55153 | 12/1998 |
| WO | WO 01 27622 | 4/2001 |
| WO | WO 01 28990 | 4/2001 |
| WO | WO 01 34563 | 5/2001 |
| WO | WO 02 00617 | 1/2002 |
| WO | WO 02/16310 | 2/2002 |
| WO | WO 2005/000794 | 1/2005 |

OTHER PUBLICATIONS

Souillac et al. Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. Advanced Drug Delivery Reviews, 48 (2001), pp. 3-26.*
U.S. Appl. No. 09/935,044, filed Aug. 23, 2001, Dalton et al.
U.S. Appl. No. 09/935,045, filed Aug. 23, 2001, Dalton et al.
U.S. Appl. No. 09/644,970, filed Aug. 2, 2000, Dalton et al.
U.S. Appl. No. 10/298,229, filed Nov. 28, 2002, Miller et al.
U.S. Appl. No. 10/270,232, filed Oct. 15, 2002, Dalton et al.
U.S. Appl. No. 10/277,108, filed Oct. 23, 2002, Dalton et al.
U.S. Appl. No. 10/270,732, filed Oct. 15, 2002, Dalton et al.
Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.
Berger et al., "Concepts and limitations in the application of radiolabeled antiandrogens, estrogens, or androgens as isotropic scanning agents for the prostate", Invest Urol, (1975), 1391, 10-16.

(Continued)

*Primary Examiner* — Jennifer M Kim
(74) *Attorney, Agent, or Firm* — Mark S. Cohen; Pearl Cohen Zedek Latzer, LLP

(57) ABSTRACT

This invention provides: 1) a method of treating a subject suffering from a muscle wasting disorder; 2) a method of preventing a muscle wasting disorder in a subject; 3) a method of treating, preventing, suppressing, inhibiting or reducing muscle loss in a subject suffering from a muscle wasting disorder; 4) a method of treating, preventing, inhibiting, reducing or suppressing muscle wasting in a subject suffering from a muscle wasting disorder; and/or 5) a method of treating, preventing, inhibiting, reducing or suppressing muscle protein catabolism in a subject suffering from a muscle wasting disorder, by administering to the subject a selective androgen receptor modulator (SARM) and/or an analog, derivative, isomer, metabolite, pharmaceutically acceptable salt, pharmaceutical product, hydrate, N-oxide, prodrug, polymorph, impurity or crystal of said SARM compound, or any combination thereof.

48 Claims, 12 Drawing Sheets

OTHER PUBLICATIONS

Howard Tucker and Glynne J. Chesterson, J. Med Chem. 1988, 31, pp. 885-887, "Resolution of the Nonsteroidal Antiandrogen—4'-Cyano-3-[(4-fluorophenyl)sulfonyl]-2-hydroxy-2-methyl-3'-(trifluoromethyl)-propionanilide and the Determination of the Absolute Configuration of the Active Enantiomer".

D. McKillop, et al., "Enantioselective metabolism and pharmacokinetics of Casodex in the male rat", Xenobiotica, 1995, vol. 25, No. 6, 623-634.

Leonid Kirkovsky, et al., "[$^{125}$I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.

David T. Baird and Anna F. Glasier, "Hormonal Contraception—Drug Therapy", The New England Journal of Medicine, May 27, 1993. pp. 1543-1549.

F.C. W. Wu. "Male Contraception: Current Status and Future Prospects", Clinical Endocrinology, (1988), 29, pp. 443-465.

World Health Organisation Task Force on Methods for the Regulation of Male Fertility, "Contraceptive efficacy of testosterone-induced azoospermia in normal men", The Lancet, vol. 336, Oct. 20, 1990, pp. 955-959 and 1517-1518.

C. G. Francisco, et al., "Long-acting contraceptive agents: testosterone esters of unsaturated acids", Steroids, Jan. 1990, vol. 55, Butterworths.

John M. Hoberman and Charles E. Yesalis, "The History of Synthetic Testosterone", Scientific American, Feb. 1995, pp. 76-81.

Leonid Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.

Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4-(trifluoromethyl)-2H-pyrano[3,2-g]quinolin-2-one. Bioorg. Med. Chem. Lett., 9: 1003, 1999.

Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.

Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3,4-diaklyl-1,2,3,4-tetrahydro-8-pyridono[5,6-g]quinolines: potent, nonsteroidal androgen receptor agonists. Bioorg. Med. Chem. Lett., 9:1335, 1999.

Hamann LG, Mani NS, Davis RL., Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210, 1999.

Rosen J, Day A, Jones TK, Jones ET, Nadzan AM, and Stein RB. Intracellular receptors and signal transducers and activators of transcription superfamilies: novel targets for small-molecule drug discovery. J. Med. Chem.. 38: 4855, 1995.

Dalton JT, Mukherjee A, Zhu Z, Kirkovsky L, and Miller DD. Discovery of Nonsteroidal Androgens. Biochem. Biophys. Res. Commun.,244(1 ):1-4, 1998.

Edwards JP, West SJ, Pooley CLF, Marschke KB, Farmer LJ, and Jones TK. New nonsteroidal androgen receptor modulators based on 4-(trifluoromethyl)-2-(1H)-Pyrololidino[3,2-g]quinolone. Bioorg. Med. Chem. Lett., 8: 745, 1998.

Buchwald, et Long-term, continuous intravenous heparin administration by an implantable infusion pump in ambulatory patients with recurrent venous thrombosis.Surgery, 1980 88(4):507-16.

Goodson, et al (1984) Medical Applications of Controlled Release vol. 2, 115-138.

Langer, et al New methods of drug delivery. Science. Sep. 28, 1990; 249(4976):1527-33. Review.

Saudek, et al A preliminary trial of the programmable implantable medication system for insulin delivery. N Engl J Med. Aug. 31, 1989; 321(9):574-9.

Treat, et al (1989) Liposomes in the Therapy of Infectious Disease and Cancer 353-365.

Handelsman, DJ, "Bridging the gender gap in contraception: another hurdle cleared", The Medical Journal of Australia, vol. 154, Feb. 18, 1996, p. 230-233.

La Spada AR, Wilson EM, Lubahn DB, Harding AE, Fischbeck KH. "Androgen receptor gene mutations in X-linked spinal and bulbar muscular atrophy." Nature. Jul 4, 1991;352(6330):77-9.

* cited by examiner

Effects of Compound V on skeletal muscle of rat

* p<0.05 when compared to untreated control

Figure 3 - Intact
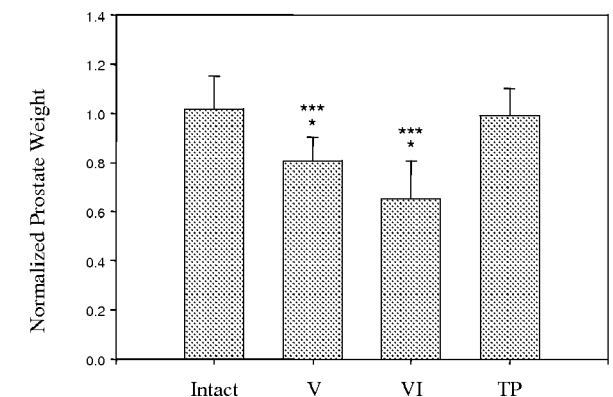
A
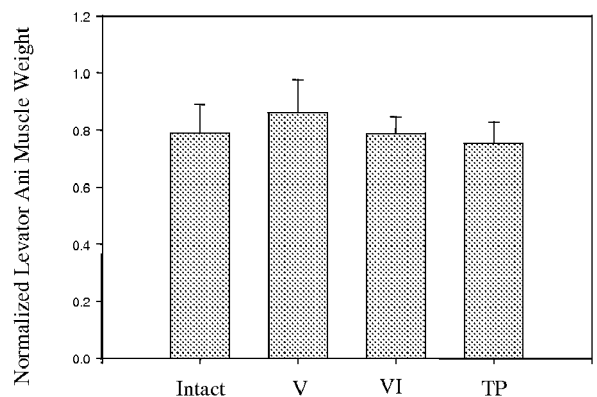
B
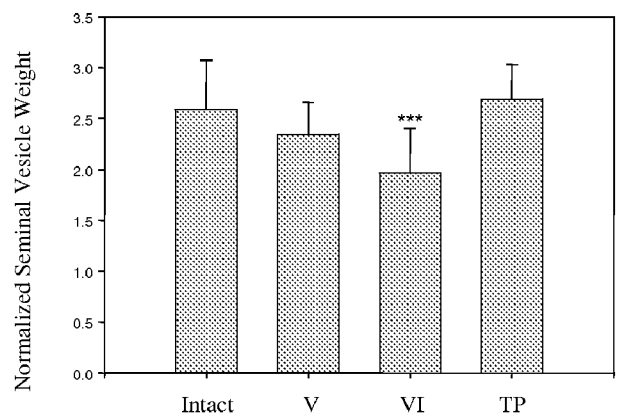
C
\* Compared to intact control, p<0.05
\*\*\* Compard to TP group, p<0.05

Figure 4 - Hemi-orchidectomized
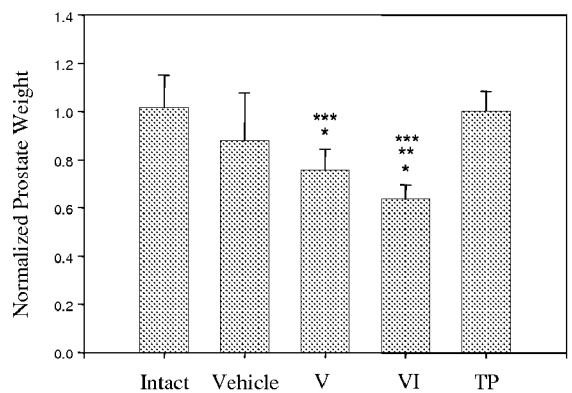
A
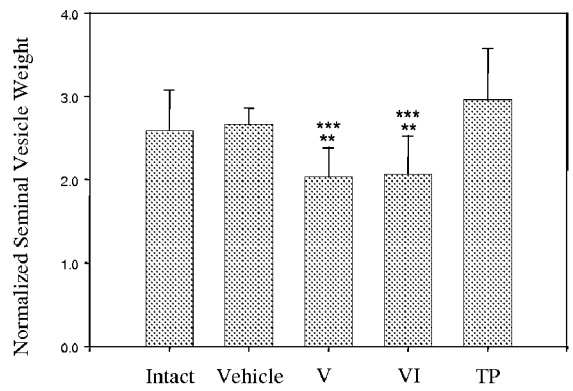
B
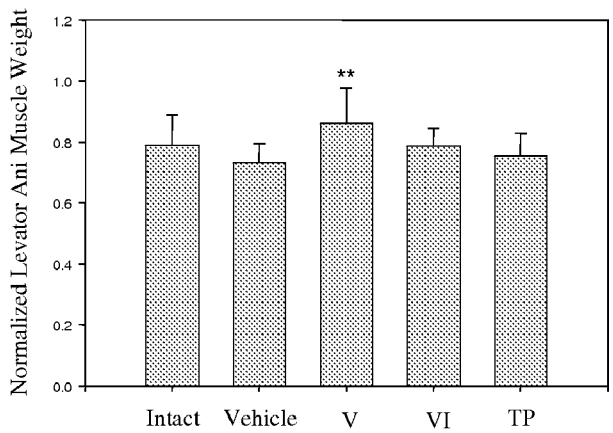
C
\* Compared to intact control, p<0.05
\*\* Compared to vehicle control, p<0.05
\*\*\* Compard to TP group, p<0.05

Figure 5 - Castrated
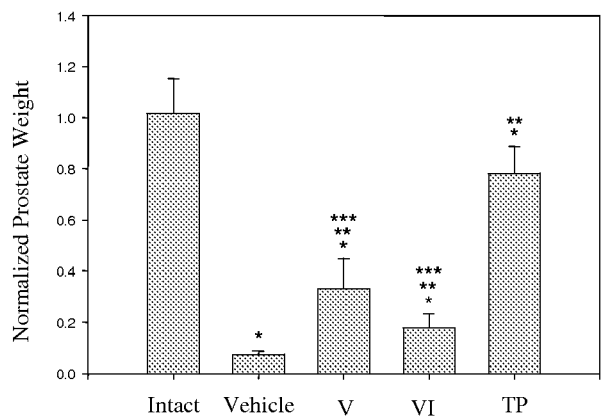
A
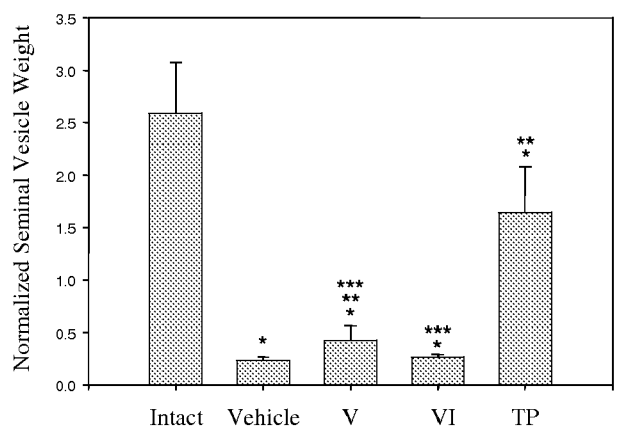
B
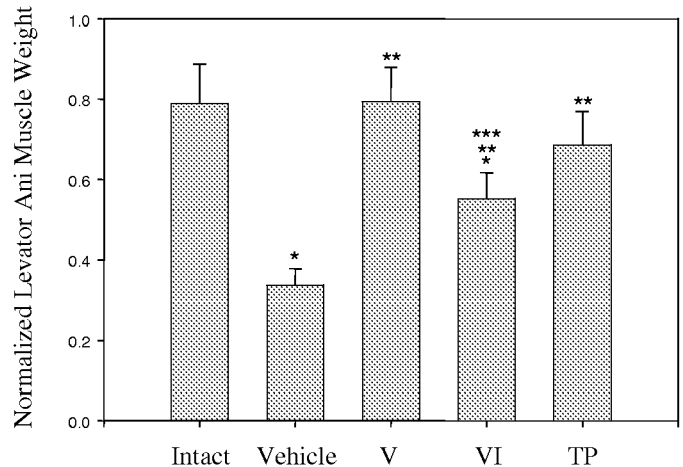
C
\* Compared to intact control, p<0.05
\*\* Compared to vehicle control, p<0.05
\*\*\* Compard to TP group, p<0.05

(A)
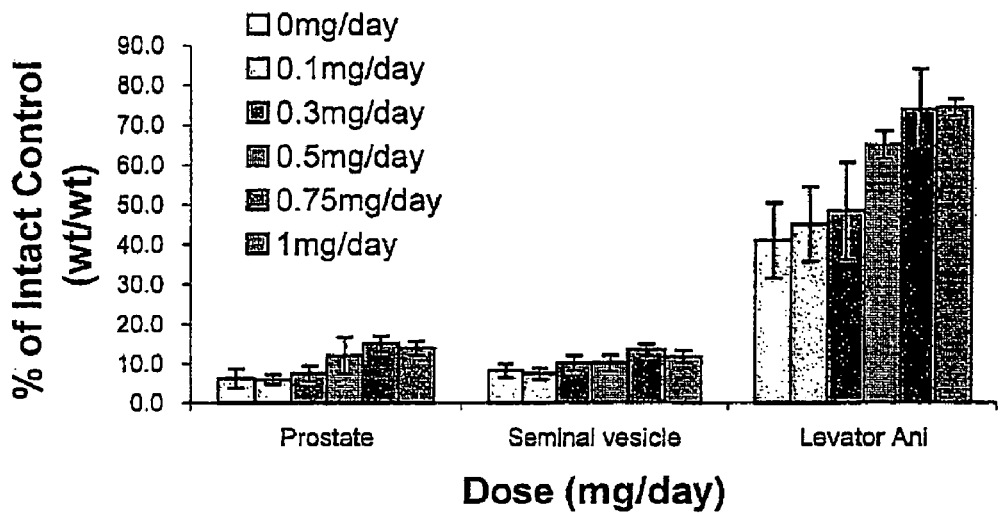
(B)
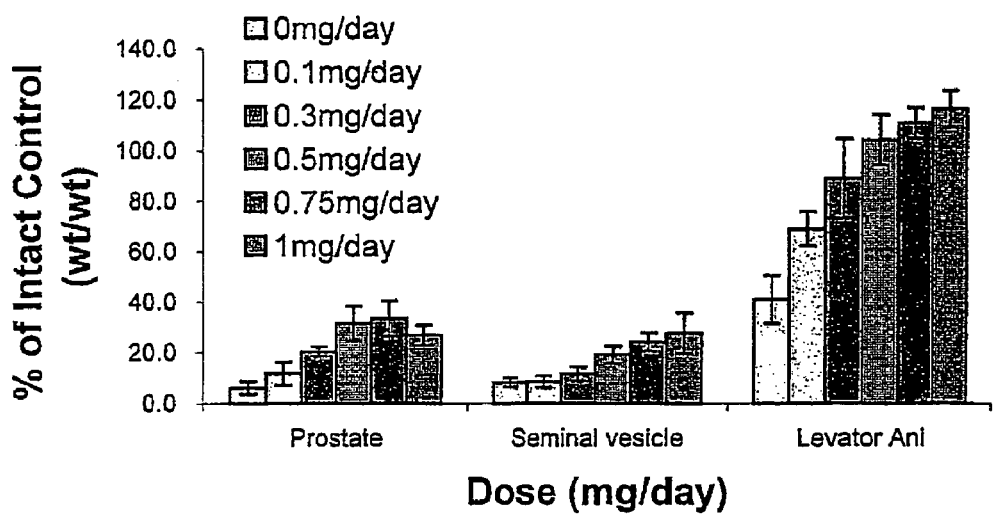
FIGURE 7 (i)

(C)
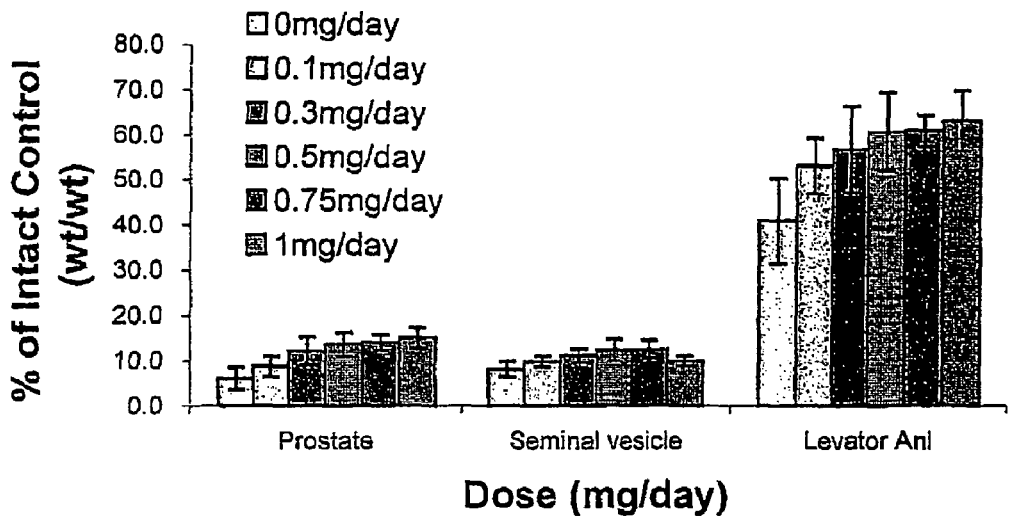
(D)
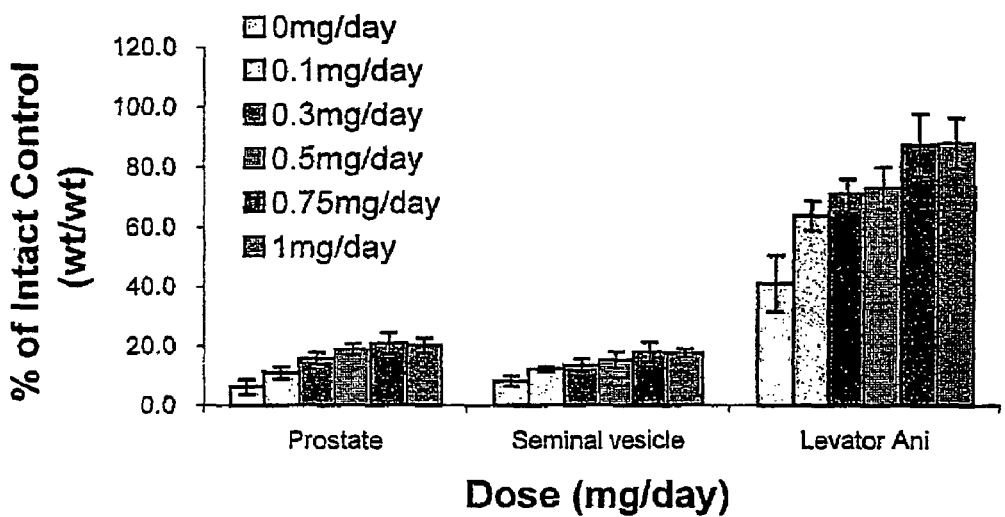
FIGURE 7 (ii)

SEQUENCE LISTING

<160> NUMBER OF SEQ ID NOS: 4

<210> SEQ ID NO 1
<211> LENGTH: 19
<212> TYPE: DNA
<213> ORGANISM: Homo sapiens

<400> SEQUENCE: 1
gaaggccaag aaggccatc                                           19

<210> SEQ ID NO 2
<211> LENGTH: 20
<212> TYPE: DNA
<213> ORGANISM: Homo sapiens

<400> SEQUENCE: 2
gtgtgatttc ttctgtcacc                                          20

<210> SEQ ID NO 3
<211> LENGTH: 20
<212> TYPE: DNA
<213> ORGANISM: Homo sapiens

<400> SEQUENCE: 3
ggtcactttc ctgctttgga                                          20

<210> SEQ ID NO 4
<211> LENGTH: 20
<212> TYPE: DNA
<213> ORGANISM: Homo sapiens

<400> SEQUENCE: 4
gcggcctcct caagatgcgt                                          20

TREATING MUSCLE WASTING WITH SELECTIVE ANDROGEN RECEPTOR MODULATORS

CROSS REFERENCE TO RELATED APPLICATIONS

This application is a Continuation-In-Part Application of U.S. Ser. No. 10/310,150, filed Dec. 5, 2002, now U.S. Pat. No. 7,547,728, which claims the benefit of Provisional Application Ser. No. 60/336,185, filed Dec. 6, 2001, which is incorporated in its entirety by reference herein.

FIELD OF INVENTION

This invention relates to the prevention and treatment of muscle wasting disorders. More particularly, this invention relates to a method of treating, preventing, suppressing, inhibiting, or reducing the incidence of muscle wasting in a subject suffering from a muscle wasting disorder, by administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity or crystal, or any combination thereof.

BACKGROUND OF THE INVENTION

Muscle wasting refers to the progressive loss of muscle mass and/or to the progressive weakening and degeneration of muscles, including the skeletal or voluntary muscles, which control movement, cardiac muscles, which control the heart (cardiomyopathics), and smooth muscles. Chronic muscle wasting is a chronic condition (i.e. persisting over a long period of time) characterized by progressive loss of muscle mass, weakening and degeneration of muscle.

The loss of muscle mass that occurs during muscle wasting can be characterized by a muscle protein degradation by catabolism. Protein catabolism occurs because of an unusually high rate of protein degradation, an unusually low rate of protein synthesis, or a combination of both. Muscle protein catabolism, whether caused by a high degree of protein degradation or a low degree of protein synthesis, leads to a decrease in muscle mass and to muscle wasting.

Muscle wasting is associated with chronic, neurological, genetic or infectious pathologies, diseases, illnesses or conditions. These include Muscular Dystrophies such as Duchenne Muscular Dystrophy and Myotonic Dystrophy; Muscle Atrophies such as Post-Polio Muscle Atrophy (PPMA); Cachexias such as Cardiac Cachexia, AIDS Cachexia and Cancer Cachexia, malnutrition, Leprosy, Diabetes, Renal Disease, Chronic Obstructive Pulmonary Disease (COPD), Cancer, end stage Renal failure, Sarcopenia, Emphysema, Osteomalacia, HIV Infection, AIDS, and Cardiomyopathy.

In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism.

An intact androgen receptor (AR) signaling pathway is crucial for appropriate development of skeletal muscles. Furthermore, an intact AR-signalling pathway increases lean muscle mass, muscle strength and muscle protein synthesis.

Muscle wasting, if left unabated, can have dire health consequences. For example, the changes that occur during muscle wasting can lead to a weakened physical state that is detrimental to an individual's health, resulting in increased susceptibility to infraction and poor performance status. In addition, muscle wasting is a strong predictor of morbidity and mortality in patients suffering from cachexia and AIDS. Innovative approaches are urgently needed at both the basic science and clinical levels to prevent and treat muscle wasting, in particular chronic muscle wasting. The present invention is directed to satisfying this need.

SUMMARY OF THE INVENTION

This invention provides: 1) a method of treating a subject suffering from a muscle wasting disorder; 2) a method of preventing a muscle wasting disorder in a subject; 3) a method of treating, preventing, suppressing, inhibiting or reducing muscle loss in a subject suffering from a muscle wasting disorder; 4) a method of treating, preventing, inhibiting, reducing or suppressing muscle wasting in a subject suffering from a muscle wasting disorder; and/or 5) a method of treating, preventing, inhibiting, reducing or suppressing muscle protein catabolism in a subject suffering from a muscle wasting disorder, by administering to the subject a selective androgen receptor modulator (SARM) and/or an analog, derivative, isomer, metabolite, pharmaceutically acceptable salt, pharmaceutical product, hydrate, N-oxide, prodrug, polymorph, impurity or crystal of said SARM compound, or any combination thereof.

Thus, in one embodiment, the present invention provides a method of treating a subject suffering from a muscle wasting disorder, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

In another embodiment, the present invention provides a method of preventing a muscle wasting disorder in a subject, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

In another embodiment, the present invention provides a method of treating, preventing, suppressing, inhibiting or reducing muscle loss in a subject suffering from a muscle wasting disorder, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

In another embodiment, the present invention provides a method of treating, preventing, inhibiting, reducing or suppressing muscle wasting in a subject suffering from a muscle wasting disorder, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

In another embodiment, the present invention provides a method of treating, preventing, inhibiting, reducing or suppressing muscle protein catabolism in a subject suffering from a muscle wasting disorder, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

In one embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula I and/or its analog, derivative, isomer, metabolite, pharmaceutically acceptable salt, pharmaceutical product, hydrate, N-oxide, impurity, prodrug, polymorph, crystal, or any combination thereof:

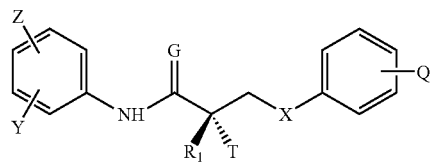

I wherein G is O or S;
X is a bond, O, $CH_2$, NH, Se, PR, NO or NR;
T is OH, OR, —$NHCOCH_3$, or NHCOR
Z is $NO_2$, CN, COOH, COR, NHCOR or CONHR;
Y is $CF_3$, F, I, Br, Cl, CN, $CR_3$ or $SnR_3$;
Q is alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

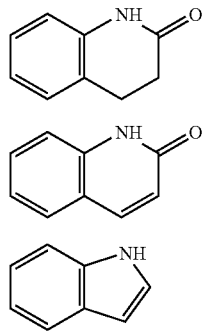

A

B

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula II and/or its analog, derivative, isomer, metabolite, pharmaceutically acceptable salt, pharmaceutical product, hydrate, N-oxide, impurity, prodrug, polymorph, crystal; or any combination thereof:

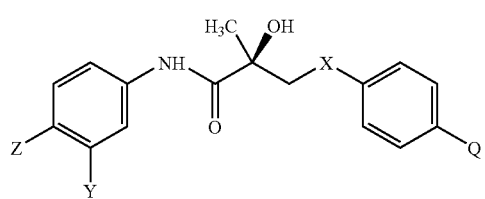

II wherein X is a bond, O, $CH_2$, NH, Se, PR, NO or NR;
Z is $NO_2$, CN, COOH, COR, NHCOR or CONHR;
Y is $CF_3$, F, I, Br, Cl, CN, $CR_3$ or $SnR_3$;
Q is alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

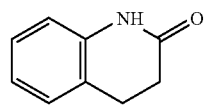

A

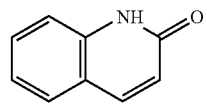

B

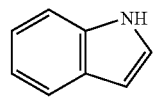

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH.

In one embodiment, the SARM compound is a compound of formula II wherein X is O. In another embodiment, the SARM compound is a compound of formula II wherein Y is $CF_3$. In another embodiment, the SARM compound is a compound of formula II wherein Z is $NO_2$. In another embodiment, the SARM compound is a compound of formula II wherein Z is CN. In another embodiment, the SARM compound is a compound of formula II wherein Q is halogen. i.e. F, Cl, Br or I. In another embodiment, the SARM compound is a compound of formula II wherein Q is $NHCOCH_3$.

In another embodiment, the SARM compound is a compound of formula II wherein X is O, Z is $NO_2$, Y is $CF_3$ and Q is halogen. In another embodiment, the SARM compound is a compound of formula II wherein X is O, Z is $NO_2$, Y is $CF_3$ and Q is $NHCOCH_3$. In another embodiment, the SARM compound is a compound of formula II wherein X is O, Z is CN, Y is $CF_3$ and Q is halogen. In another embodiment, the SARM compound is a compound of formula II wherein X is O, Z is CN, Y is $CF_3$ and Q is $NHCOCH_3$.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula III and/or its analog, derivative, isomer, metabolite, pharmaceutically acceptable salt, pharmaceutical product, hydrate, N-oxide, impurity, prodrug, polymorph, crystal, or any combination thereof:

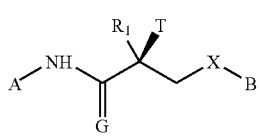

III wherein X is a bond, O, CH$_2$, NH, Se, PR, NO or NR;
G is O or S;
R$_1$ is CH$_3$, CH$_2$F, CHF$_2$, CF$_3$, CH$_2$CH$_3$, or CF$_2$CF$_3$;
T is OH, OR, —NHCOCH$_3$, or NHCOR;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;
A is a ring selected from:

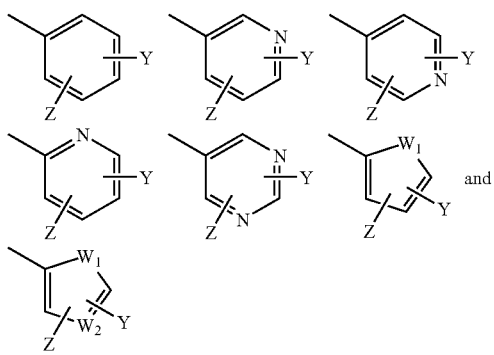

B is a ring selected from:

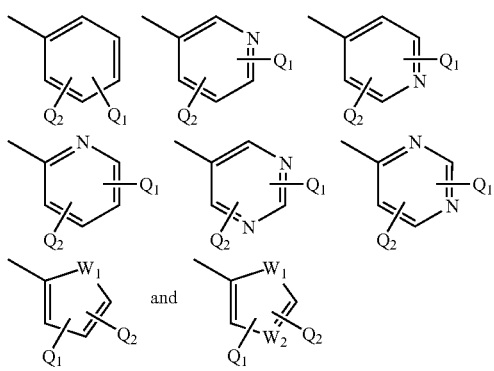

wherein A and B cannot simultaneously be a benzene ring;
Z is NO$_2$, CN, COOH, COR, NHCOR or CONHR;
Y is CF$_3$, F, I, Br, Cl, CN CR$_3$ or SnR$_3$;
Q$_1$ and Q$_2$ are independently of each other a hydrogen, alkyl, halogen, CF$_3$, CN CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R, SR,

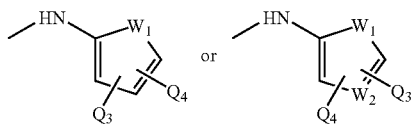

Q$_3$ and Q$_4$ are independently of each other a hydrogen, alkyl, halogen, CF$_3$, CN CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR;
W$_1$ is O, NH, NR, NO or S; and
W$_2$ is N or NO.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula IV and/or its analog, derivative, isomer, metabolite, pharmaceutically acceptable salt, pharmaceutical product, hydrate, N-oxide, impurity, prodrug, polymorph, crystal, or any combination thereof:

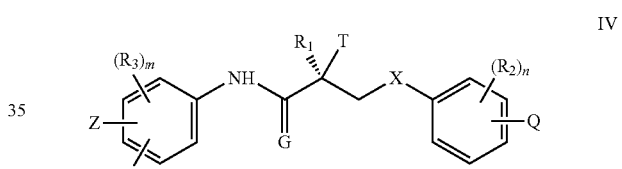

IV wherein X is a bond, O, CH$_2$, NH, Se, PR, NO or NR;
G is O or S;
T is OH, OR, —NHCOCH$_3$, or NHCOR;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;
R$_1$ is CH$_3$, CH$_2$F, CHF$_2$, CF$_3$, CH$_2$CH$_3$, or CF$_2$CF$_3$;
R$_2$ is F, Cl, Br, I, CH$_3$, CF$_3$, OH, CN, NO$_2$, NHCOCH$_3$, NHCOCF$_3$, NHCOR, alkyl, arylalkyl, OR, NH$_2$, NHR, NR$_2$, SR;
R$_3$ is F, Cl, Br, I, CN, NO$_2$, COR, COOH, CONHR, CF$_3$, SnR$_3$, or R$_3$ together with the benzene ring to which it is attached forms a fused ring system represented by the structure:

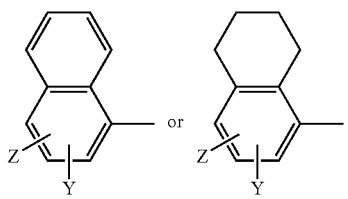

Z is NO$_2$, CN, COR, COOH, or CONHR;
Y is CF$_3$, F, Br, Cl, I, CN, or SnR$_3$;
Q is H, alkyl, halogen, CF$_3$, CN CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OH, OR, COR, OCOR, OSO$_2$R, SO$_2$R, SR; or Q together with the benzene ring to which it is attached is a fused ring system represented by structure A, B or C:

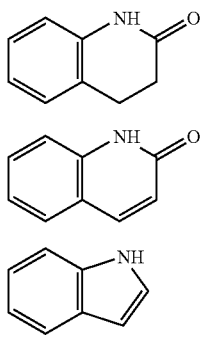

n is an integer of 1-4; and
m is an integer of 1-3.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula V and/or its analog, derivative, isomer, metabolite, pharmaceutically acceptable salt, pharmaceutical product, hydrate, N-oxide, impurity, prodrug, polymorph, crystal, or any combination thereof:

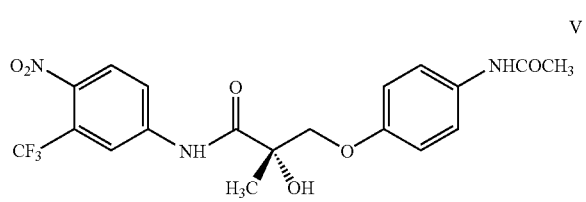

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula VI and/or its analog, derivative, isomer, metabolite, pharmaceutically acceptable salt, pharmaceutical product, hydrate, N-oxide, impurity, prodrug, polymorph, crystal, or any combination thereof:

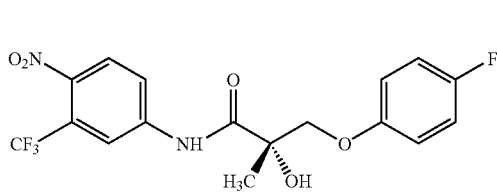

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula VII and/or its analog, derivative, isomer, metabolite, pharmaceutically acceptable salt, pharmaceutical product, hydrate, N-oxide, impurity, prodrug, polymorph, crystal, or any combination thereof:

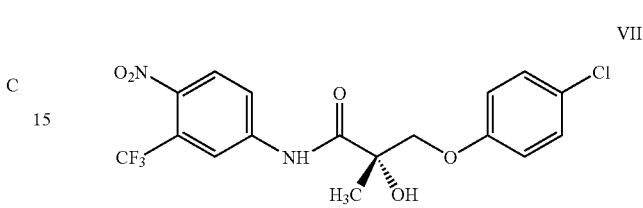

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or, suppressing muscle wasting due to a muscle wasting disorder; and/or 5) treating, preventing, inhibiting, reducing or suppressing muscle protein catabolism due to a muscle wasting disorder, is a compound represented by the structure of formula VIII and/or its analog, derivative, isomer, metabolite, pharmaceutically acceptable salt, pharmaceutical product, hydrate, N-oxide, impurity, prodrug, polymorph, crystal, or any combination thereof:

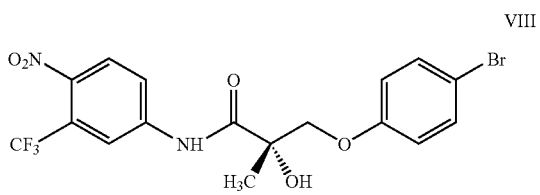

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula IX and/or its analog, derivative, isomer, metabolite, pharmaceutically acceptable salt, pharmaceutical product, hydrate, N-oxide, impurity, prodrug, polymorph, crystal, or any combination thereof:

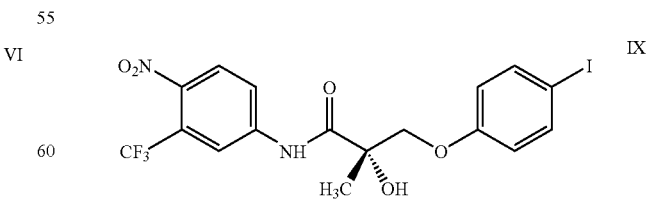

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula X and/or its analog, derivative, isomer, metabolite, pharmaceutically acceptable salt, pharmaceutical product, hydrate, N-oxide, impurity, prodrug, polymorph, crystal, or any combination thereof:

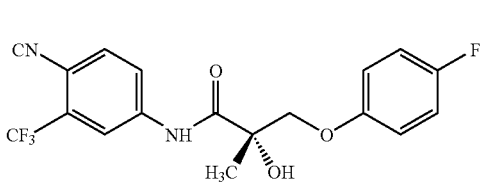

X

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula XI and/or its analog, derivative, isomer, metabolite, pharmaceutically acceptable salt, pharmaceutical product, hydrate, N-oxide, impurity, prodrug, polymorph, crystal, or any combination thereof:

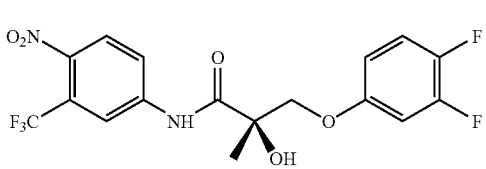

XI

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula XII and/or its analog, derivative, isomer, metabolite, pharmaceutically acceptable salt, pharmaceutical product, hydrate, N-oxide, impurity, prodrug, polymorph, crystal, or any combination thereof:

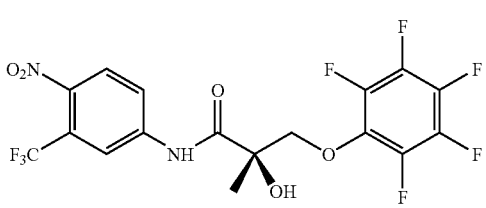

XII

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula XIII and/or its analog, derivative, isomer, metabolite, pharmaceutically acceptable salt, pharmaceutical product, hydrate, N-oxide, impurity, prodrug, polymorph, crystal, or any combination thereof:

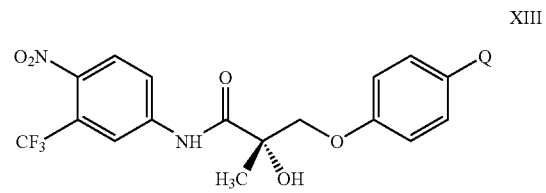

XIII wherein Q is as defined above for formula I.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula XIV and/or its analog, derivative, isomer, metabolite, pharmaceutically acceptable salt, pharmaceutical product, hydrate, N-oxide, impurity, prodrug, polymorph, crystal, or any combination thereof:

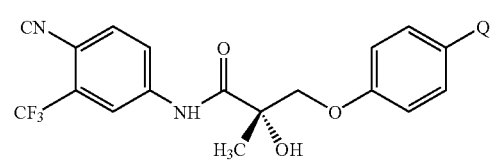

XIV wherein Q is as defined above for formula I.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula XV and/or its analog, derivative, isomer, metabolite, pharmaceutically acceptable salt, pharmaceutical product, hydrate, N-oxide, impurity, prodrug, polymorph, crystal, or any combination thereof:

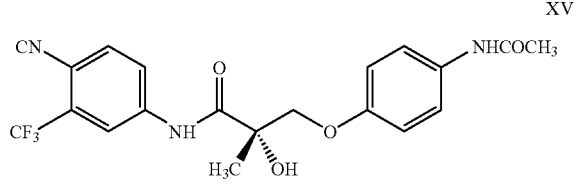

XV

In one embodiment, the administration comprises administering a pharmaceutical composition comprising the SARM, and a pharmaceutically acceptable carrier.

In one embodiment, the muscle wasting disorder is due to a pathology, illness, disease or condition. In another embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious.

In another embodiment, the pathology, illness, disease or condition is a Muscular Dystrophy, a Muscular Atrophy, X-linked spinal-bulbar Muscular Atrophy (SBMA), a Cachexia, malnutrition, Leprosy, Diabetes, Renal Disease, Chronic Obstructive Pulmonary Disease (COPD), Cancer, end stage Renal failure, Sarcopenia, Emphysema, Osteomalacia, HIV Infection, AIDS, or Cardiomyopathy.

In another embodiment, the muscle wasting disorder is an age-associated muscle wasting disorder, a disuse deconditioning associated muscle wasting disorder, or the muscle wasting disorder occurs due to chronic lower back pain, burns, central nervous system (CNS) injury or damage, peripheral nerve injury or damage, spinal cord injury or damage, chemical injury or damage, or alcoholism. In another embodiment, the muscle wasting disorder is a chronic muscle wasting disorder.

The present invention provides a safe and effective method for treating, preventing, suppressing, inhibiting or reducing loss of muscle due to muscle wasting and is particularly useful for treating subjects with a muscle wasting disorder, for example a chronic muscle wasting disorder.

BRIEF DESCRIPTION OF THE DRAWINGS

FIG. 3: Androgenic and Anabolic activity of Compounds V and VI in rats. Male rats with normal testicular function (no surgical manipulation) were left untreated (Intact), treated with compound V (0.5 mg/day), compound VI (0.5 mg/day) or testosterone proprionate (TP, 0.5 mg/day), and the weight of androgen-responsive tissues (prostate—FIG. 3A, semimal vesicles—FIG. 3B, and levator ani muscle—FIG. 3C) were determined.

FIG. 4: Androgenic and Anabolic activity of Compounds V and VI in rats. Male rats received unilateral orchidectomy (Hemi-orchidectomized) and were left untreated (Intact), treated with vehicle alone (PEG 300), Compound V (0.5 mg/day), Compound VI (0.5 mg/day), or testosterone proprionate (TP, 0.5 mg/day), and the weight of androgen-responsive tissues (prostate—FIG. 4A, semimal vesicles—FIG. 4B, and levator ani muscle—FIG. 4C) were determined.

FIG. 5: Androgenic and Anabolic activity of Compounds V and VI in rats. Male rats received bilateral orchidectomy (Castrated) and were left untreated (Intact), treated with vehicle alone (PEG 300), Compound V (0.5 mg/day), Compound VI (0.5 mg/day), or testosterone proprionate (TP, 0.5 mg/day), and the weight of androgen-responsive tissues (prostate—FIG. 5A, semimal vesicles—FIG. 5B, and levator ani muscle—FIG. 5C) were determined.

FIG. 7: Dose response curves of Compounds VI-IX in rats. Rats were left untreated, or treated with 0.1, 0.3, 0.5, 0.75 and 1 mg/day of Compound VI (A), Compound VII (B), Compound VIII (C) or Compound IX (D), and the weights of androgen-responsive tissues (prostate and semimal vesicles) and levator ani muscle were determined.

DETAILED DESCRIPTION OF THE INVENTION

Figure 1A:
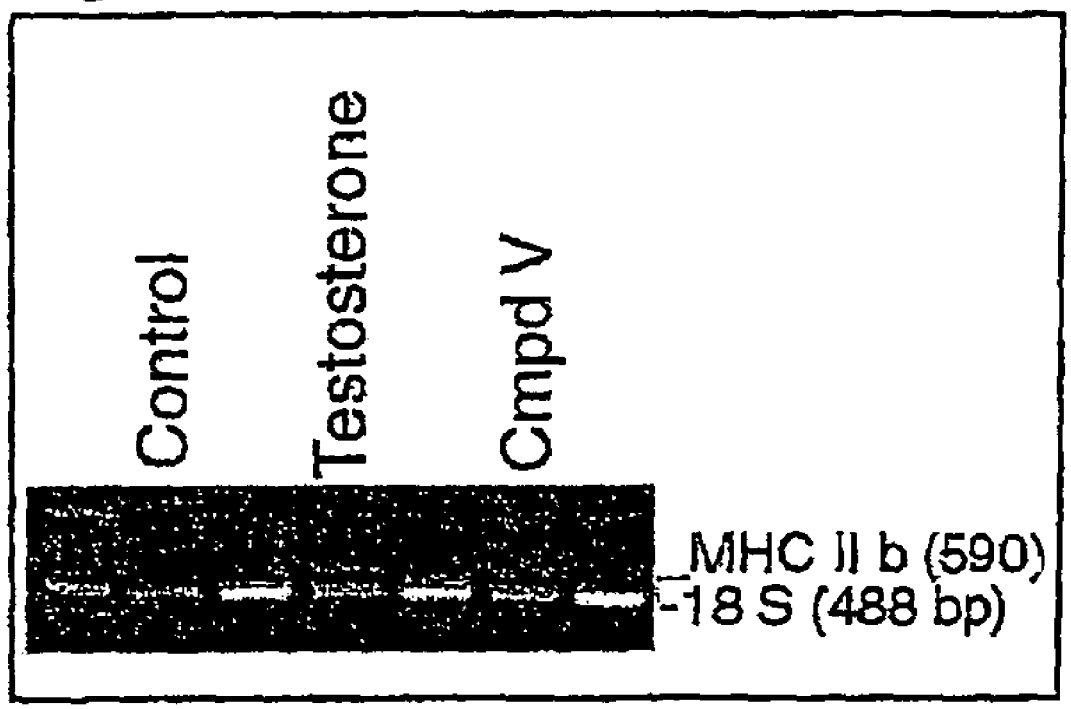
FIG. 1: Effect of androgens on MHC IIb mRNA expression from masseter muscle in female rats. A) MHC IIb transcript (590 bp) resolved on 1.2% agarose gel with internal control 18S mRNA (488 bp); B) Histogram analysis of control (C, no drug treatment), testosterone propionate (TP), and compound V.

This invention provides: 1) a method of treating a subject suffering from a muscle wasting disorder; 2) a method of preventing a muscle wasting disorder in a subject; 3) a method of treating, preventing, suppressing, inhibiting or reducing muscle loss in a subject suffering from a muscle wasting disorder; 4) a method of treating, preventing, inhibiting, reducing or suppressing muscle wasting in a subject suffering from a muscle wasting disorder; and/or 5) a method of treating, preventing, inhibiting, reducing or suppressing muscle protein catabolism in a subject suffering from a muscle wasting disorder, by administering to the subject a selective androgen receptor modulator (SARM) and/or an analog, derivative, isomer, metabolite, pharmaceutically acceptable salt, pharmaceutical product, hydrate, N-oxide, prodrug, polymorph, impurity or crystal of said SARM compound, or any combination thereof.

Thus, in one embodiment, the present invention provides a method of treating a subject suffering from a muscle wasting disorder, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

In another embodiment, the present invention provides a method of preventing a muscle wasting disorder in a subject, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

In another embodiment, the present invention provides a method of treating, preventing, suppressing, inhibiting or reducing muscle loss in a subject suffering from a muscle wasting disorder, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

In another embodiment, the present invention provides a method of treating, preventing, inhibiting, reducing or suppressing muscle wasting in a subject suffering from a muscle wasting disorder, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

In another embodiment, the present invention provides a method of treating, preventing, inhibiting, reducing or suppressing muscle protein catabolism in a subject suffering from a muscle wasting disorder, comprising the step of administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity, crystal or any combination thereof.

Selective Androgen Receptor Modulators (SARMS)

Selective androgen receptor modulators (SARMs) are a class of androgen receptor targeting agents (ARTA), which demonstrate androgenic and anabolic activity of a nonsteroidal ligand for the androgen receptor. These novel agents are useful in males for the treatment of a variety of hormone-related conditions such as sexual dysfunction, decreased sexual libido, erectile dysfunction, hypogonadism, sarcopenia, osteopenia, osteoporosis, alterations in cognition and mood, depression, anemia, hair loss, obesity, benign prostate hyperplasia and/or prostate cancer. Further, SARMs are useful for oral testosterone replacement therapy, and imaging prostate cancer. In addition, SARMs are useful in females for the treatment of a variety of hormone-related conditions including, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer.

In one embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula I:

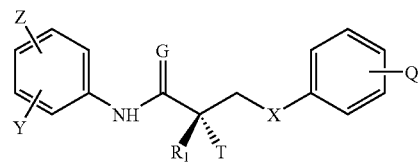

I wherein G is O or S;
X is a bond, O, CH$_2$, NH, Se, PR, NO or NR;
T is OH, OR, —NHCOCH$_3$, or NHCOR
Z is NO$_2$, CN, COOH, COR, NHCOR or CONHR;
Y is CF$_3$, F, I, Br, Cl, CN, CR$_3$ or SnR$_3$;
Q is alkyl, halogen, CF$_3$, CN CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

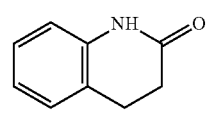

A

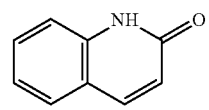

B

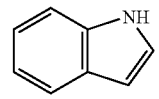

C

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is CH$_3$, CH$_2$F, CHF$_2$, CF$_3$, CH$_2$CH$_3$, or CF$_2$CF$_3$.

In one embodiment, the SARM is an analog of the compound of formula I. In another embodiment, the SARM is a derivative of the compound of formula I. In another embodiment, the SARM is an isomer of the compound of formula I. In another embodiment, the SARM is a metabolite of the compound of formula I. In another embodiment, the SARM is a pharmaceutically acceptable salt of the compound of formula I. In another embodiment, the SARM is a pharmaceutical product of the compound of formula I. In another embodiment, the SARM is a hydrate of the compound of formula I. In another embodiment, the SARM is an N-oxide of the compound of formula I. In another embodiment, the SARM is a crystal of the compound of formula I. In another embodiment, the SARM is a polymorph of the compound of formula I. In another embodiment, the SARM is an impurity of the compound of formula I. In another embodiment, the SARM is a prodrug of the compound of formula I. In another embodiment, the SARM is a combination of any of an analog, derivative, metabolite, isomer, pharmaceutically acceptable salt, pharmaceutical product, hydrate, N-oxide, crystal, impurity, polymorph or prodrug of the compound of formula I.

In one embodiment, the SARM compound is a compound of formula I wherein X is O. In one embodiment, the SARM compound is a compound of formula I wherein G is O. In another embodiment, the SARM compound is a compound of formula I wherein Z is $NO_2$. In another embodiment, the SARM compound is a compound of formula I wherein Z is CN. In another embodiment, the SARM compound is a compound of formula I wherein Y is $CF_3$. In another embodiment, the SARM compound is a compound of formula I wherein Q is $NHCOCH_3$. In another embodiment, the SARM compound is a compound of formula I wherein Q is F. In another embodiment, the SARM compound is a compound of formula I wherein T is OH. In another embodiment, the SARM compound is a compound of formula I wherein $R_1$ is $CH_3$.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula II:

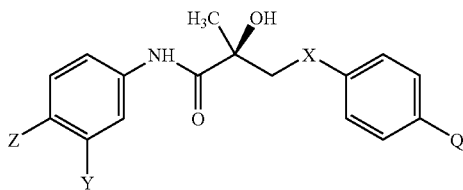

II wherein X is a bond, O, $CH_2$, NH, Se, PR, NO or NR;
Z is $NO_2$, CN, COOH, COR, NHCOR or CONHR;
Y is $CF_3$, F, I, Br, Cl, CN, $CR_3$ or $SnR_3$;
Q is alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

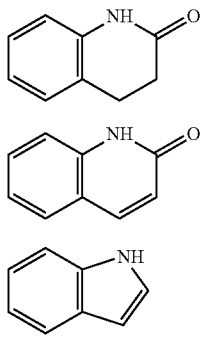

A

B

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH.

In one embodiment, the SARM is an analog of the compound of formula II. In another embodiment, the SARM is a derivative of the compound of formula II. In another embodiment, the SARM is an isomer of the compound of formula II. In another embodiment, the SARM is a metabolite of the compound of formula II. In another embodiment, the SARM is a pharmaceutically acceptable salt of the compound of formula II. In another embodiment, the SARM is a pharmaceutical product of the compound of formula II. In another embodiment, the SARM is a hydrate of the compound of formula II. In another embodiment, the SARM is an N-oxide of the compound of formula II. In another embodiment, the SARM is a crystal of the compound of formula II. In another embodiment, the SARM is a polymorph of the compound of formula II. In another embodiment, the SARM is an impurity of the compound of formula II. In another embodiment, the SARM is a prodrug of the compound of formula II. In another embodiment, the SARM is a prodrug of the compound of formula II. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula II.

In one embodiment, the SARM compound is a compound of formula II wherein X is O. In another embodiment, the SARM compound is a compound of formula II wherein Z is $NO_2$. In another embodiment, the SARM compound is a compound of formula II wherein Z is CN. In another embodiment, the SARM compound is a compound of formula II wherein Y is $CF_3$. In another embodiment, the SARM compound is a compound of formula II wherein Q is $NHCOCH_3$. In another embodiment, the SARM compound is a compound of formula II wherein Q is F. In another embodiment, the SARM compound is a compound of formula II where Q is halogen, i.e. F, Cl, Br or I.

In another embodiment, the SARM compound is a compound of formula II wherein X is O, Z is $NO_2$, Y is $CF_3$ and Q is halogen. In another embodiment, the SARM compound is a compound of formula II wherein X is O, Z is $NO_2$, Y is $CF_3$ and Q is $NHCOCH_3$. In another embodiment, the SARM compound is a compound of formula II wherein X is O, Z is CN, Y is $CF_3$ and Q is halogen. In another embodiment, the SARM compound is a compound of formula II wherein X is O, Z is CN, Y is $CF_3$ and Q is $NHCOCH_3$.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula III:

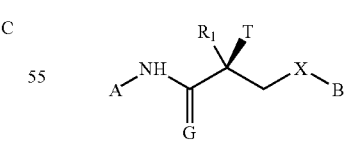

III wherein X is a bond, O, $CH_2$, NH, Se, PR, NO or NR;
G is O or S;
$R_1$ is $CH_3$, $CH_2F$, $CHF_2$, $CF_3$, $CH_2CH_3$, or $CF_2CF_3$;
T is OH, OR, —$NHCOCH_3$, or NHCOR;
R is alkyl, haloalkyl, dihaloalkyl, trihaloalkyl, $CH_2F$, $CHF_2$, $CF_3$, $CF_2CF_3$, aryl, phenyl, halogen, alkenyl or OH;

A is a ring selected from:

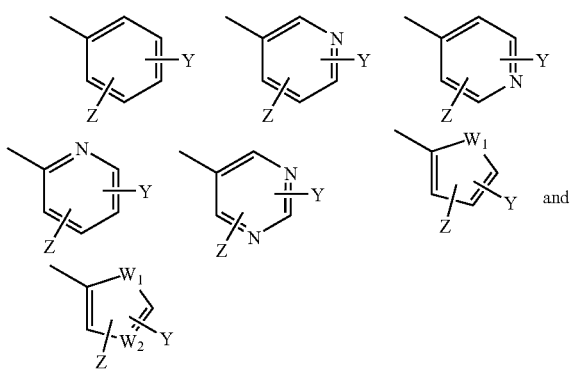

B is a ring selected from:

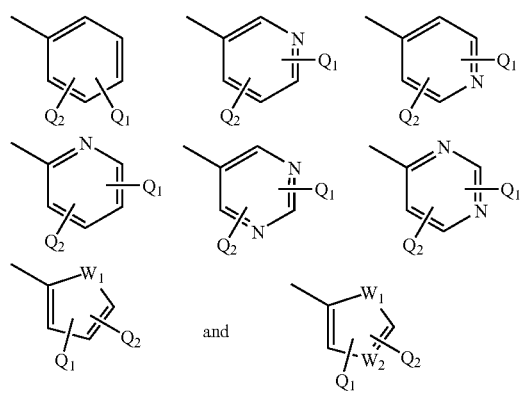

wherein A and B cannot simultaneously be a benzene ring;

Z is $NO_2$, CN, COOH, COR, NHCOR or CONHR;

Y is $CF_3$, F, I, Br, Cl, CN $CR_3$ or $SnR_3$;

$Q_1$ and $Q_2$ are independently of each other a hydrogen, alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR,

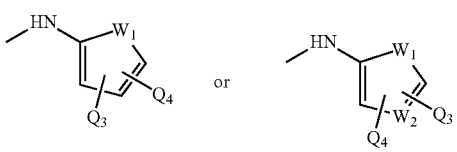

$Q_3$ and $Q_4$ are independently of each other a hydrogen, alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR;

$W_1$ is O, NH, NR, NO or S; and $W_2$ is N or NO.

In one embodiment, the SARM is an analog of the compound of formula III. In another embodiment, the SARM is a derivative of the compound of formula III. In another embodiment, the SARM is an isomer of the compound of formula III. In another embodiment, the SARM is a metabolite of the compound of formula III. In another embodiment, the SARM is a pharmaceutically acceptable salt of the compound of formula III. In another embodiment, the SARM is a pharmaceutical product of the compound of formula III. In another embodiment, the SARM is a hydrate of the compound of formula III. In another embodiment, the SARM is an N-oxide of the compound of formula III. In another embodiment, the SARM is a crystal of the compound of formula III. In another embodiment, the SARM is a polymorph of the compound of formula III. In another embodiment, the SARM is a prodrug of the compound of formula III. In another embodiment, the SARM is an impurity of the compound of formula III. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula III.

In one embodiment, the SARM compound is a compound of formula III wherein X is O. In another embodiment, the SARM compound is a compound of formula III wherein G is O. In another embodiment, the SARM compound is a compound of formula I wherein T is OH. In another embodiment, the SARM compound is a compound of formula III wherein $R_1$ is $CH_3$. In another embodiment, the SARM compound is a compound of formula III wherein Z is $NO_2$. In another embodiment, the SARM compound is a compound of formula III wherein Z is CN. In another embodiment, the SARM compound is a compound of formula III wherein Y is $CF_3$. In another embodiment, the SARM compound is a compound of formula III wherein $Q_1$ is $NHCOCH_3$. In another embodiment, the SARM compound is a compound of formula III wherein $Q_1$ is F.

The substituents Z and Y can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents $Q_1$ and $Q_2$ can be in any position of the ring carrying these substituents (hereinafter "B ring"). In one embodiment, the substitutent $Q_1$ is in the para position of the B ring. In another embodiment, the subsituent is $Q_2$ is H. In another embodiment, the substitutent $Q_1$ is in the para position of the B ring and the subsituent is $Q_2$ is H. In another embodiment, the substitutent $Q_1$ is $NHCOCH_3$ and is in the para position of the B ring, and the substituent is $Q_2$ is H.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula IV:

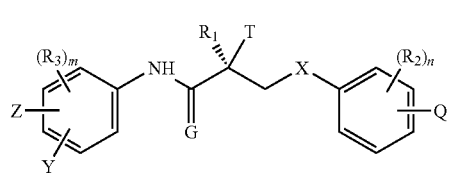

wherein X is a bond, O, $CH_2$, NH, Se, PR, NO or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

$R_1$ is $CH_3$, $CH_2F$, $CHF_2$, $CF_3$, $CH_2CH_3$, or $CF_2CF_3$;

$R_2$ is F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $NR_2$, SR;

$R_3$ is F, Cl, Br, I, CN, $NO_2$, COR, COOH, CONHR, $CF_3$, $SnR_3$, or $R_3$ together with the benzene ring to which it is attached forms a fused ring system represented by the structure:

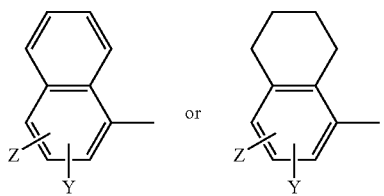

Z is $NO_2$, CN, COR, COOH, or CONHR;
Y is $CF_3$, F, Br, Cl, I, CN, or $SnR_3$;
Q is H, alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OH, OR, COR, OCOR, $OSO_2R$, $SO_2R$, SR; or Q together with the benzene ring to which it is attached is a fused ring system represented by structure A, B or C:

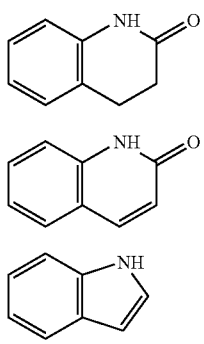

n is an integer of 1-4; and
m is an integer of 1-3.

In one embodiment, the SARM is an analog of the compound of formula IV. In another embodiment, the SARM is a derivative of the compound of formula IV. In another embodiment, the SARM is an isomer of the compound of formula IV. In another embodiment, the SARM is a metabolite of the compound of formula IV. In another embodiment, the SARM is a pharmaceutically acceptable salt of the compound of formula IV. In another embodiment, the SARM is a pharmaceutical product of the compound of formula IV. In another embodiment, the SARM is a hydrate of the compound of formula IV. In another embodiment, the SARM is an N-oxide of the compound of formula IV. In another embodiment, the SARM is a crystal of the compound of formula IV. In another embodiment, the SARM is a polymorph of the compound of formula IV. In another embodiment, the SARM is a prodrug of the compound of formula IV. In another embodiment, the SARM is an impurity of the compound of formula IV. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula IV.

In one embodiment, the SARM compound is a compound of formula IV wherein X is O. In another embodiment, the SARM compound is a compound of formula IV wherein G is O. In another embodiment, the SARM compound is a compound of formula IV wherein Z is $NO_2$. In another embodiment, the SARM compound is a compound of formula IV wherein Z is CN. In another embodiment, the SARM compound is a compound of formula IV wherein Y is $CF_3$. In another embodiment, the SARM compound is a compound of formula IV wherein Q is $NHCOCH_3$. In another embodiment, the SARM compound is a compound of formula IV wherein Q is F. In another embodiment, the SARM compound is a compound of formula IV wherein T is OH. In another embodiment, the SARM compound is a compound of formula IV wherein $R_1$ is $CH_3$. In another embodiment, the SARM compound is a compound of formula IV wherein Q is F and $R_2$ is $CH_3$. In another embodiment, the SARM compound is a compound of formula IV wherein Q is F and $R_2$ is Cl.

The substituents Z, Y and $R_3$ can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents Q and $R_2$ can be in any position of the ring carrying these substituents (hereinafter "B ring"). In one embodiment, the substitutent Q is in the para position of the B ring. In another embodiment, the substitutent Q is in the para position of the B ring. In another embodiment, the substitutent Q is $NHCOCH_3$ and is in the para position of the B ring.

As contemplated herein, when the integers m and n are greater than one, the substituents $R_2$ and $R_3$ are not limited to one particular substituent, and can be any combination of the substituents listed above.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula V:

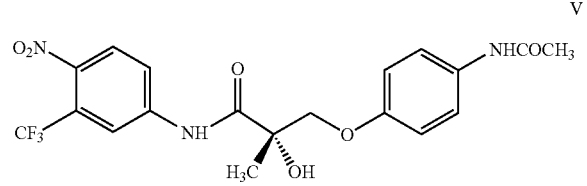

In one embodiment, the SARM is an analog of the compound of formula V. In another embodiment, the SARM is a derivative of the compound of formula V. In another embodiment, the SARM is an isomer of the compound of formula V. In another embodiment, the SARM is a metabolite of the compound of formula V. In another embodiment, the SARM is a pharmaceutically acceptable salt of the compound of formula V. In another embodiment, the SARM is a pharmaceutical product of the compound of formula V. In another embodiment, the SARM is a hydrate of the compound of formula V. In another embodiment, the SARM is an N-oxide of the compound of formula V. In another embodiment, the SARM is a crystal of the compound of formula V. In another embodiment, the SARM is a polymorph of the compound of formula V. In another embodiment, the SARM is an impurity of the compound of formula V. In another embodiment, the SARM is a prodrug of the compound of formula V. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula V.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula VI:

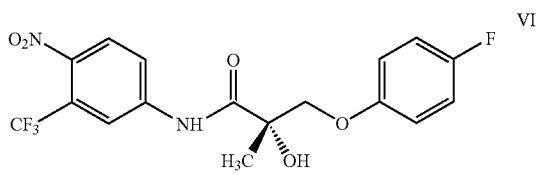

In one embodiment, the SARM is an analog of the compound of formula VI. In another embodiment, the SARM is a derivative of the compound of formula VI. In another embodiment, the SARM is an isomer of the compound of formula VI. In another embodiment, the SARM is a metabolite of the compound of formula VI. In another embodiment, the SARM is a pharmaceutically acceptable salt of the compound of formula VI. In another embodiment, the SARM is a pharmaceutical product of the compound of formula VI. In another embodiment, the SARM is a hydrate of the compound of formula VI. In another embodiment, the SARM is an N-oxide of the compound of formula VI. In another embodiment, the SARM is a crystal of the compound of formula VI. In another embodiment, the SARM is a polymorph of the compound of formula VI. In another embodiment, the SARM is an impurity of the compound of formula VI. In another embodiment, the SARM is a prodrug of the compound of formula VI. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula VI.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula VII:

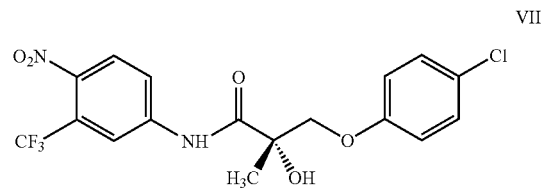

In one embodiment, the SARM is an analog of the compound of formula VII. In another embodiment, the SARM is a derivative of the compound of formula VII. In another embodiment, the SARM is an isomer of the compound of formula VII. In another embodiment, the SARM is a metabolite of the compound of formula VII. In another embodiment, the SARM is a pharmaceutically acceptable salt of the compound of formula VII. In another embodiment, the SARM is a pharmaceutical product of the compound of formula VII. In another embodiment, the SARM is a hydrate of the compound of formula VII. In another embodiment, the SARM is an N-oxide of the compound of formula VII. In another embodiment, the SARM is a crystal of the compound of formula VII. In another embodiment, the SARM is a polymorph of the compound of formula VII. In another embodiment, the SARM is an impurity of the compound of formula VII. In another embodiment, the SARM is a prodrug of the compound of formula VII. In another embodiment, the SARM is a combination of any of an analog, derivative, metabolite, isomer, pharmaceutically acceptable salt, pharmaceutical product, hydrate, N-oxide, crystal, polymorph, impurity or prod rug of the compound of formula VII.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula VIII:

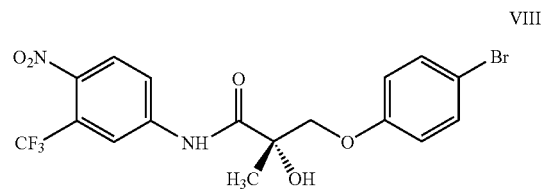

In one embodiment, the SARM is an analog of the compound of formula VIII. In another embodiment, the SARM is a derivative of the compound of formula VIII. In another embodiment, the SARM is an isomer of the compound of formula VIII. In another embodiment, the SARM is a metabolite of the compound of formula VIII. In another embodiment, the SARM is a pharmaceutically acceptable salt of the compound of formula VIII. In another embodiment, the SARM is a pharmaceutical product of the compound of formula VIII. In another embodiment, the SARM is a hydrate of the compound of formula VIII. In another embodiment, the SARM is an N-oxide of the compound of formula VIII. In another embodiment, the SARM is a crystal of the compound of formula VIII. In another embodiment, the SARM is a polymorph of the compound of formula VIII. In another embodiment, the SARM is an impurity of the compound of formula VIII. In another embodiment, the SARM is a prodrug of the compound of formula VIII. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula VIII.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula IX:

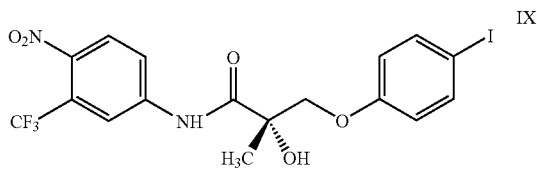

In one embodiment, the SARM is an analog of the compound of formula IX. In another embodiment, the SARM is a derivative of the compound of formula IX. In another embodiment, the SARM is an isomer of the compound of formula IX. In another embodiment, the SARM is a metabolite of the compound of formula IX. In another embodiment, the SARM is a pharmaceutically acceptable salt of the compound of formula IX. In another embodiment, the SARM is a pharmaceutical product of the compound of formula IX. In another embodiment, the SARM is a hydrate of the compound of formula IX. In another embodiment, the SARM is an N-oxide of the compound of formula IX. In another embodiment, the SARM is a crystal of the compound of formula IX. In another embodiment, the SARM is a polymorph of the compound of formula IX. In another embodiment, the SARM is an impurity of the compound of formula IX. In another embodiment, the SARM is a prodrug of the compound of formula IX. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula IX.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula X:

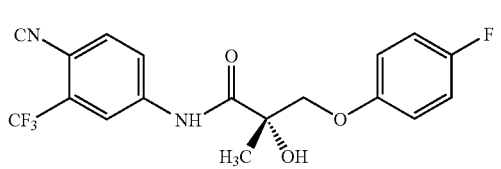

In one embodiment, the SARM is an analog of the compound of formula X. In another embodiment, the SARM is a derivative of the compound of formula X. In another embodiment, the SARM is an isomer of the compound of formula X. In another embodiment, the SARM is a metabolite of the compound of formula X. In another embodiment, the SARM is a pharmaceutically acceptable salt of the compound of formula X. In another embodiment, the SARM is a pharmaceutical product of the compound of formula X. In another embodiment, the SARM is a hydrate of the compound of formula X. In another embodiment, the SARM is an N-oxide of the compound of formula X. In another embodiment, the SARM is a crystal of the compound of formula X. In another embodiment, the SARM is a polymorph of the compound of formula X. In another embodiment, the SARM is an impurity of the compound of formula X. In another embodiment, the SARM is a prodrug of the compound of formula X. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula X.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula XI:

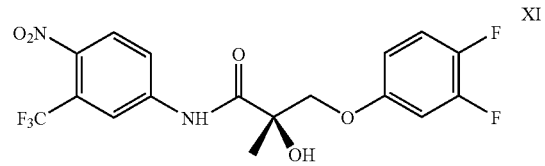

In one embodiment, the SARM is an analog of the compound of formula XI. In another embodiment, the SARM is a derivative of the compound of formula XI. In another embodiment, the SARM is an isomer of the compound of formula XI. In another embodiment, the SARM is a metabolite of the compound of formula XI. In another embodiment, the SARM is a pharmaceutically acceptable salt of the compound of formula XI. In another embodiment, the SARM is a pharmaceutical product of the compound of formula XI. In another embodiment, the SARM is a hydrate of the compound of formula XI. In another embodiment, the SARM is an N-oxide of the compound of formula XI. In another embodiment, the SARM is a crystal of the compound of formula XI. In another embodiment, the SARM is a polymorph of the compound of formula XI. In another embodiment, the SARM is an impurity of the compound of formula XI. In another embodiment, the SARM is a prodrug of the compound of formula XI. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula XI.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula XII:

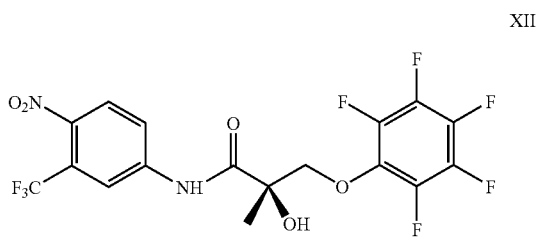

XII

In one embodiment, the SARM is an analog of the compound of formula XII. In another embodiment, the SARM is a derivative of the compound of formula XII. In another embodiment, the SARM is an isomer of the compound of formula XII. In another embodiment, the SARM is a metabolite of the compound of formula XII. In another embodiment, the SARM is a pharmaceutically acceptable salt of the compound of formula XII. In another embodiment, the SARM is a pharmaceutical product of the compound of formula XII. In another embodiment, the SARM is a hydrate of the compound of formula XII. In another embodiment, the SARM is an N-oxide of the compound of formula XII. In another embodiment, the SARM is a crystal of the compound of formula XII. In another embodiment, the SARM is a polymorph of the compound of formula XII. In another embodiment, the SARM is an impurity of the compound of formula XII. In another embodiment, the SARM is a prodrug of the compound of formula XII. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula XII.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula XIII:

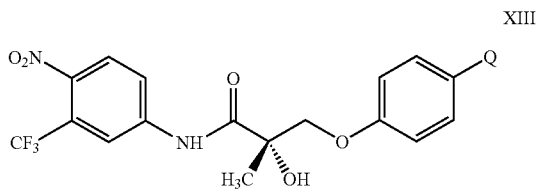

XIII wherein Q is as defined above for formula I.

In one embodiment, the SARM is an analog of the compound of formula XIII. In another embodiment, the SARM is a derivative of the compound of formula XIII. In another embodiment, the SARM is an isomer of the compound of formula XIII. In another embodiment, the SARM is a metabolite of the compound of formula XIII. In another embodiment, the SARM is a pharmaceutically acceptable salt of the compound of formula XIII. In another embodiment, the SARM is a pharmaceutical product of the compound of formula XIII. In another embodiment, the SARM is a hydrate of the compound of formula XIII. In another embodiment, the SARM is an N-oxide of the compound of formula XIII. In another embodiment, the SARM is a crystal of the compound of formula XIII. In another embodiment, the SARM is a polymorph of the compound of formula XIII. In another embodiment, the SARM is an impurity of the compound of formula XIII. In another embodiment, the SARM is a prodrug of the compound of formula XIII. In another embodiment, the SARM is a combination of any of an analog, derivative, Metabolite, isomer, pharmaceutically acceptable salt, pharmaceutical product, hydrate, N-oxide, crystal, polymorph, impurity or prodrug of the compound of formula XIII.

In one embodiment, the SARM is a compound of formula XIII wherein Q is F. In another embodiment, the SARM is a compound of formula XIII wherein Q is Cl. In another embodiment, the SARM is a compound of formula XIII wherein Q is Br. In another embodiment, the SARM is a compound of formula XIII wherein Q is I. In another embodiment, the SARM is a compound of formula XIII wherein Q is $NHCOCH_3$.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound of formula XIV:

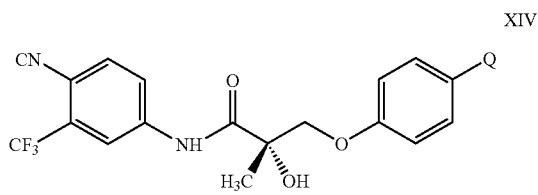

XIV wherein Q is as defined above for formula I.

In one embodiment, the SARM is an analog of the compound of formula XIV. In another embodiment, the SARM is a derivative of the compound of formula XIV. In another embodiment, the SARM is an isomer of the compound of formula XIV. In another embodiment, the SARM is a metabolite of the compound of formula XIV. In another embodiment, the SARM is a pharmaceutically acceptable salt of the compound of formula XIV. In another embodiment, the SARM is a pharmaceutical product of the compound of formula XIV. In another embodiment, the SARM is a hydrate of the compound of formula XIV. In another embodiment, the SARM is an N-oxide of the compound of formula XIV. In another embodiment, the SARM is a crystal of the compound of formula XIV. In another embodiment, the SARM is a polymorph of the compound of formula XIV. In another embodiment, the SARM is an impurity of the compound of formula XIV. In another embodiment, the SARM is a prodrug of the compound of formula XIV. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula XIV.

In one embodiment, the SARM is a compound of formula XIV wherein Q is F. In another embodiment, the SARM is a compound of formula XIV wherein Q is Cl. In another embodiment, the SARM is a compound of formula XIV wherein Q is Br. In another embodiment, the SARM is a compound of formula XIV wherein Q is I. In another embodiment, the SARM is a compound of formula XIV wherein Q is NHCOCH$_3$.

In another embodiment, the SARM compound which is effective at 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, is a compound represented by the structure of formula XV:

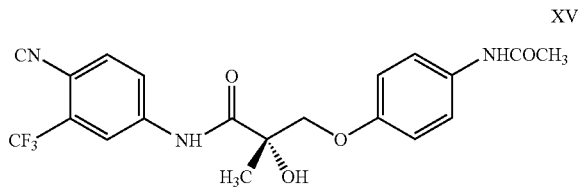

XV

In one embodiment, the SARM is an analog of the compound of formula XV. In another embodiment, the SARM is a derivative of the compound of formula XV. In another embodiment, the SARM is an isomer of the compound of formula XV. In another embodiment, the SARM is a metabolite of the compound of formula XV. In another embodiment, the SARM is a pharmaceutically acceptable salt of the compound of formula XV. In another embodiment, the SARM is a pharmaceutical product of the compound of formula XV. In another embodiment, the SARM is a hydrate of the compound of formula XV. In another embodiment, the SARM is an N-oxide of the compound of formula XV. In another embodiment, the SARM is a crystal of the compound of formula XV. In another embodiment, the SARM is a polymorph of the compound of formula XV. In another embodiment, the SARM is an impurity of the compound of formula XV. In another embodiment, the SARM is a prodrug of the compound of formula XV. In another embodiment, the SARM is a combination of any of an analog, derivative, metabolite, isomer, pharmaceutically acceptable salt, pharmaceutical product, hydrate, N-oxide, crystal, polymorph, impurity or prodrug of the compound of formula XV.

The substituent R in the SARM compounds of the present invention is defined herein as an alkyl, haloalkyl, dihaloalkyl, trihaloalkyl, CH$_2$F, CHF$_2$, CF$_3$, CF$_2$CF$_3$, aryl, phenyl, halogen, alkenyl or OH.

An "alkyl" group refers to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

An "alkenyl" group refers to an unsaturated hydrocarbon, including straight chain, branched chain and cyclic groups having one or more double bond. The alkenyl group may have one double bond, two double bonds, three double bonds etc. Examples of alkenyl groups are ethenyl, propenyl, butenyl, cyclohexenyl etc. The alkenyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, e.g. by F, Cl, Br or I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. It is understood by a person skilled in the art that when T in the compounds of the present invention is OR, R is not OH. A halo group refers to F, Cl, Br or I.

An "arylalkyl" group refers to an alkyl bound to an aryl, wherein alkyl and aryl are as defined above. An example of an arylalkyl group is a benzyl group.

As contemplated herein, the present invention relates to the use of a SARM compound and/or an analog, derivative, isomer, metabolite, pharmaceutically acceptable salt, pharmaceutical product, hydrate, N-oxide, prodrug, polymorph, impurity or crystal or combinations thereof. In one embodiment, the invention relates to the use of an analog of the SARM compound. In another embodiment, the invention relates to the use of a derivative of the SARM compound. In another embodiment, the invention relates to the use of an isomer of the SARM compound. In another embodiment, the invention relates to the use of a metabolite of the SARM compound. In another embodiment, the invention relates to the use of a pharmaceutically acceptable salt of the SARM compound. In another embodiment, the invention relates to the use of a pharmaceutical product of the SARM compound. In another embodiment, the invention relates to the use of a hydrate of the SARM compound. In another embodiment, the invention relates to the use of an N-oxide of the SARM compound. In another embodiment, the invention relates to the use of a prodrug of the SARM compound. In another embodiment, the invention relates to the use of a polymorph of the SARM compound. In another embodiment, the invention relates to the use of a crystal of the SARM compound in another embodiment, the invention relates to the use of an impurity of the SARM compound. In another embodiment, the invention relates to the use of any of a combination of an analog, derivative, isomer, metabolite, pharmaceutically acceptable salt, pharmaceutical product, hydrate, N-oxide, prodrug, polymorph, impurity or crystal of the SARM compounds of the present invention.

In one embodiment, the term "isomer" includes, but is not limited to, optical isomers and analogs, structural isomers and analogs, conformational isomers and analogs, and the like.

In one embodiment, this invention encompasses the use of various optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes derivatives of the SARM compounds in one embodiment, "derivatives" includes but is not limited to ether derivatives, acid derivatives, amide derivatives, ester derivatives and the like. In addition, this invention further includes hydrates of the SARM compounds. In one embodiment, "hydrate" includes but is not limited to hemihydrate, monohydrate, dihydrate, trihydrate and the like.

This invention further includes metabolites of the SARM compounds. In one embodiment, "metabolite" means any substance produced from another substance by metabolism or a metabolic process.

This invention further includes pharmaceutical products of the SARM compounds. The term "pharmaceutical product" means a composition suitable for pharmaceutical use (pharmaceutical composition), as defined herein.

Biological Activity of Selective Androgen Modulator Compounds

As contemplated herein, the SARM compounds of the present invention as useful in treating, preventing, suppressing, inhibiting or reducing the incidence of muscle wasting disorders, as defined herein. An intact androgen receptor (AR) signaling pathway is crucial for appropriate development of skeletal muscles. Furthermore, an intact AR-signalling pathway increases lean muscle mass, muscle strength and muscle protein synthesis.

A muscle is a tissue of the body that primarily functions as a source of power. There are three types of muscles in the body: a) skeletal muscle—the muscle responsible for moving extremities and external areas of the bodies; b) cardiac muscle—the heart muscle; and c) smooth muscle—the muscle that is in the walls of arteries and bowel.

A wasting condition or disorder is defined herein as a condition or disorder that is characterized, at least in part, by an abnormal, progressive loss of body, organ or tissue mass. A wasting condition can occur as a result of a pathology such as, for example, cancer, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

These include but are not limited to Muscular Dystrophies; Muscle Atrophies; Cachexias; malnutrition, Leprosy, Diabetes, Renal Disease, Chronic Obstructive Pulmonary Disease (COPD), Cancer, end stage Renal failure, Sarcopenia, Emphysema, Osteomalacia, HIV Infection, AIDS, or Cardiomyopathy.

In another embodiment, the muscle wasting disorder is due to an infectious disease such as enterovirus, Epstein-Barr virus, herpes zoster, HIV, trypanosomiasis, influenze, coxsacke, infectious mononucleosis, Rickettsia, Trichinella, or Schistosomiasis.

The muscular dystrophies are genetic diseases characterized by progressive weakness and degeneration of the skeletal or voluntary muscles that control movement. The muscles of the heart and some other involuntary muscles are also affected in some forms of muscular dystrophy. The major forms of Muscular Dystrophy are: Duchenne Muscular Dystrophy, Myotonic Dystrophy, Duchenne Muscular Dystrophy, Becker Muscular Dystrophy, Limbgirdle Muscular Dystrophy, Facioscapulhumeral Muscular Dystrophy, Congenital Muscular Dystrophy, Oculopharyngeal Muscular Dystrophy, Distal Muscular Dystrophy and Emery-Dreifuss Muscular Dystrophy.

Muscular Dystrophy can affect people of all ages. Although some forms first become apparent in infancy or childhood, others may not appear until middle age or later. Duchenne Muscular Dystrophy is the most common kind of Muscular Dystrophy affecting children. Myotonic Dystrophy is the most common of these diseases in adults.

Muscle Atrophy is characterized by wasting away or diminution of muscle and a decrease in muscle mass. For example, Post-Polio Muscular Atrophy is a muscle wasting that occurs as part of the Post-Polio Syndrome (PPS). The Atrophy includes weakness, muscle fatigue, and pain.

Another type of Muscular Atrophy is X-linked spinal-bulbar Muscular Atrophy (SBMA—also known as Kennedy's Disease). This disease arises from a defect in the androgen receptor gene on the X chromosome, affects only males, and its onset is in adulthood. Because the primary disease cause is an androgen receptor mutation, androgen replacement is not a current therapeutic strategy. There are some investigational studies where exogenous testosterone propionate is being given to boost the levels of androgen with hopes of overcoming androgen insensitivity and perhaps provide an anabolic effect. Still, use of supraphysiological levels of testosterone for supplementation will have limitations and other potentially serious complications.

Cachexia is weakness and a loss of weight caused by a disease or as a side effect of illness. Cardiac Cachexia, i.e. a muscle protein wasting of both the cardiac and skeletal muscle, is a characteristic of congestive heart failure. Cancer Cachexia is a syndrome that occurs in patients with solid tumors and hematological malignancies and is manifested by weight loss with massive depletion of both adipose tissue and lean muscle mass. Acquired Immunodeficiency Syndrome (AIDS). Cachexia is a Human Immunodeficiency Virus (HIV) associated myopathy and/or muscle weakness/wasting that is a relatively common clinical manifestation of AIDS. Individuals with HIV-associated myopathy or muscle weakness or wasting typically experience significant weight loss, generalized or proximal muscle weakness, tenderness, and muscle atrophy.

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting. Studies have shown that in patients suffering injuries, chronic illnesses, burns, trauma or cancer, who are hospitalized for long periods of time, there is a long-lasting unilateral muscle wasting, with a consequent decrease in body mass.

Injuries or damage to the Central Nervous System (CNS) are also associated with muscle wasting disorders. Injuries or damage to the CNS can be, for example, caused by diseases, trauma or chemicals. Examples are central nerve injury or damage, peripheral nerve injury or damage and spinal cord injury or damage.

Finally, alcoholism has been shown to be associated with muscle wasting disorders.

As contemplated herein, this invention provides a class of compounds which are Selective Androgen Receptor Modulator (SARM) compounds. These compounds, which are useful in preventing and treating muscle wasting disorders are classified as androgen receptor agonists (AR agonists), partial agonists or androgen receptor antagonists (AR antagonists).

A receptor agonist is a substance which binds receptors and activates them. A receptor partial agonist is a substance which binds receptor and partially activate them. A receptor antagonist is a substance which binds receptors and inactivates them. As demonstrated herein, the SARM compounds of the present invention have a tissue-selective effect, wherein one agent may be an agonist, partial agonist and/or antagonist, depending on the tissue. For example, the SARM compound may stimulate muscle tissue and at the same time inhibit prostate tissue. In one embodiment, the SARMs which are useful in treating and preventing muscle wasting disorders are AR agonists, and are, therefore, useful in binding to and activating the AR. In another embodiment, the SARMs are AR antagonists, and are, therefore, useful in binding to and inactivating the AR. Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds inhibit the growth of AR containing tissue.

In yet another embodiment, the SARM compounds of the present invention can be classified as partial AR agonist/ antagonists. The SARMs are AR agonists in some tissues, to cause increased transcription of AR-responsive genes (e.g. muscle anabolic effect). In other tissues, these compounds serve as competitive inhibitors of testosterone/DHT on the AR to prevent agonistic effects of the native androgens.

The SARM compounds of the present invention bind either reversibly or irreversibly to the androgen receptor. In one embodiment, the SARM compounds bind reversibly to the androgen receptor. In another embodiment, the SARM compounds bind irreversibly to the androgen receptor. The compounds of the present invention may contain a functional group (affinity label) that allows alkylation of the androgen receptor (i.e. covalent bond formation). Thus, in this case, the compounds bind irreversibly to the receptor and, accordingly, cannot be displaced by a steroid, such as the endogenous ligands DHT and testosterone.

The present invention provides a safe and effective method for treating, preventing, suppressing, inhibiting or reducing loss of muscle and/or muscle protein catabolism due to muscle wasting and is particularly useful for treating a subject suffering from a muscle wasting disorder. In one embodiment, the subject is a mammalian subject. In another embodiment, the subject is a human subject. In another embodiment, the subject is a male subject. In another embodiment, the subject is a female subject.

Pharmaceutical Compositions

This invention provides the use of a composition and a pharmaceutical composition for treating a subject suffering from a muscle wasting disorder; for preventing a muscle wasting disorder; for treating, preventing, suppressing, inhibiting or reducing muscle loss in a subject suffering from a muscle wasting disorder; for treating, preventing, inhibiting, reducing or suppressing muscle wasting in a subject suffering from a muscle wasting disorder; and for treating, preventing, inhibiting, reducing or suppressing muscle protein catabolism in a subject suffering from a muscle wasting disorder by administering a selective androgen receptor modulator (SARM) and/or its analog, derivative, isomer, metabolite, pharmaceutically acceptable salt, pharmaceutical product, hydrate, N-oxide, or any combination thereof; and a pharmaceutically acceptable carrier.

As used herein, "pharmaceutical composition" means a "therapeutically effective amount" of the active ingredient, i.e. the SARM compound, together with a pharmaceutically acceptable carrier or diluent. In one embodiment, a "therapeutically effective amount" as used herein refers to that amount which provides a therapeutic effect for a given condition and administration regimen.

The pharmaceutical compositions containing the SARM agent can be administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to the SARM active compound and the inert carrier or diluent, a hard gelating capsule.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the SARM agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of SARM agent over a period of time.

In another embodiment, the active compound can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose, carboxymethylcellulose), a cyclodextrin, an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled release compositions, i.e. compositions in which the SARM compound is released over a period of time after administration. Controlled or sustained release compositions include formulation in lipophilic depots (e.g. fatty acids, waxes, oils). In another embodiment, the composition is an immediate release composition, i.e. a composition in which all of the SARM compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the SARM agents or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

As defined herein, "contacting" means that the SARM compound of the present invention is introduced into a sample containing the enzyme in a test tube, flask, tissue culture, chip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In another embodiment, the term "contacting" means that the SARM compound of the present invention is introduced into a subject receiving treatment, and the SARM compound is allowed to come in contact with the androgen receptor in vivo.

As used herein, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, the methods of the present invention comprise administering a SARM compound as the sole active ingredient. However, also encompassed within the scope of the present invention are methods for 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder, which comprise administering the SARM compounds in combination with one or more therapeutic agents. These agents include, but are not limited to: LHRH analogs, reversible antiandrogens, antiestrogens, selective estrogen receptor modulators (SERMS), anticancer drugs, 5-alpha reductase inhibitors, aromatase inhibitors, progestins, other selective androgen receptor modulators (SARMS), testosterone, anabolic steroids, growth hormones or agents acting through other nuclear hormone receptors.

Thus, in one embodiment, the present invention provides compositions and pharmaceutical compositions comprising a selective androgen receptor modulator compound, in combination with an LHRH analog. In another embodiment, the present invention provides compositions and pharmaceutical compositions comprising a selective androgen receptor modulator compound, in combination with a reversible antiandrogen. In another embodiment, the present invention provides compositions and pharmaceutical compositions comprising a selective androgen receptor modulator compound, in combination with an antiestrogen. In another embodiment, the present invention provides compositions and pharmaceutical compositions comprising a selective androgen receptor modulator compound, in combination with a SERM. In another embodiment, the present invention provides compositions and pharmaceutical compositions comprising a selective androgen receptor modulator compound, in combination with an anticancer drug. In another embodiment, the present invention provides compositions and pharmaceutical compositions comprising a selective androgen receptor modulator compound, in combination with a 5-alpha reductase inhibitor. In another embodiment, the present invention provides compositions and pharmaceutical compositions comprising a selective androgen receptor modulator compound, in combination with an aromatase inhibitor. In another embodiment, the present invention provides compositions and pharmaceutical compositions comprising a selective androgen receptor modulator compound, in combination with a progestin. In another embodiment, the present invention provides compositions and pharmaceutical compositions comprising a selective androgen receptor modulator compound, in combination with another SARM. In another embodiment, the present invention provides compositions and pharmaceutical compositions comprising a selective androgen receptor modulator compound, in combination with testosterone. In another embodiment, the present invention provides compositions and pharmaceutical compositions comprising a selective androgen receptor modulator compound, in combination with an anabolic steroid. In another embodiment, the present invention provides compositions and pharmaceutical compositions comprising a selective androgen receptor modulator compound, in combination with a growth hormone. In another embodiment, the present invention provides compositions and pharmaceutical compositions comprising a selective androgen receptor modulator compound, in combination with an agent acting through other nuclear hormone receptors.

Various embodiments of dosage ranges are contemplated by this invention. The dosage may be in the range of 0.1-80 mg/day. In another embodiment, the dosage is in the range of 0.1-50 mg/day. In another embodiment, the dosage is in the range of 0.1-20 mg/day. In another embodiment, the dosage is in the range of 0.1-10 mg/day. In another embodiment, the dosage is in the range of 0.1-5 mg/day. In another embodiment, the dosage is in the range of 0.5-5 mg/day. In another embodiment, the dosage is in the range of 0.5-50 mg/day. In another embodiment, the dosage is be in the range of 5-80 mg/day. In another embodiment, the dosage is in the range of 35-65 mg/day. In another embodiment, the dosage is in the range of 35-65 mg/day. In another embodiment, the dosage is in the range of 20-60 mg/day. In another embodiment, the dosage is in the range of 40-60 mg/day. In another embodiment, the dosage is in a range of 45-60 mg/day. In another embodiment, the dosage is in the range of 40-60 mg/day. In another embodiment, the dosage is in a range of 60-120 mg/day. In another embodiment, the dosage is in the range of 120-240 mg/day. In another embodiment, the dosage is in the range of 40-60 mg/day. In another embodiment, the dosage is in a range of 240-400 mg/day. In another embodiment, the dosage is in a range of 45-60 mg/day. In another embodiment, the dosage is in the range of 15-25 mg/day. In another embodiment, the dosage is in the range of 5-10 mg/day. In another embodiment, the dosage is in the range of 55-65 mg/day. In one embodiment, the dosage is 20 mg/day. In another embodiment, the dosage is 40 mg/day. In another embodiment, the dosage is 60 mg/day.

The following examples are presented in order to more fully illustrate certain embodiments of the invention. They should in no way be construed, however, as limiting the broad scope of the invention.

Experimental Details Section

Example 1

Effect of Selective Androgen Receptor Modulators (SARMS) and Testosterone on Skeletal Muscles in Intact Female Rats Compound V (N-[4-nitro-3-trifluoromethyl)phenyl]-(2S)-3-[4-(acetylamino)phenoxy]-2-hydroxy-2-methylpropanamide), is a selective androgen receptor modulator represented by the formula:

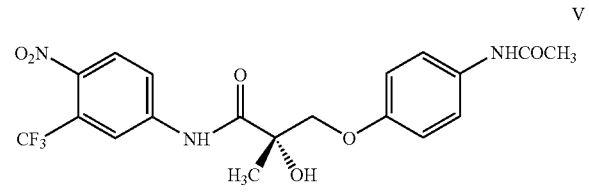

Compound V is a ligand for AR with potent binding affinity, exhibits tissue-selective androgenic and anabolic effects, and is orally bioavailable. Compound V is a powerful anabolic agent that maintains the mass of the levator ani in castrated male rats.

Myosin heavy chain (MHC) is the predominant protein in skeletal muscle encoded by a multigene family expressed in a tissue-specific and developmentally regulated manner [Adams G. R., Zeng S. A., Baldwin K. M. *Am. J. Physiol.* 276: R954-R961, 1999]. To further demonstrate the importance of compound V in muscle, the effects of this nonsteroidal anabolic agent directly in skeletal muscle by monitoring the expression of MHC subtypes using RT-PCR has been demonstrated. In steady state, mRNA expression usually parallels the pattern of MHC protein expression. Because transcription of MHC mRNA occurs in advance of MHC protein translation, and the increased sensitivity of RT-PCR compared to western blotting, rapid changes in mRNA expression can be detected and used to analyze the subtle dynamic effects of muscle anabolism [Wright C., Haddad F., Qin A. X., Baldwin K. M. *J. Appl. Phys.* 83 (4):1389-1396, 1997].

Methods:

Rat muscle tissue was harvested in 5 volumes of RNA later solution (Ambion, cat. #7020) and stored at 4° C. until used for RNA isolation. Total RNA was isolated in the FastPrep FP120 instrument (Qbiogene) using RNAqueous-4PCR kit (Ambion, cat #1914) in combination with FastRNA green tubes (Qbiogene, cat. #6040-600) at settings for time at 45 sec and speed at 6.5. 1 ug of total RNA was used for reverse transcription using Retroscript kit (Ambion, cat #1710). The mixture was incubated at 42° C. for 60 min, followed by 10 min at 92° C., and then chilled on ice and used in PCR reaction.

Relatively quantitative RT-PCR was used to analyze expression of MHC mRNA in rat musculus masseter (MM) and levator ani (LA). As an internal standard 18S ribosomal RNA was used (QuantumRNA classic 18S Internal Standard, Ambion, cat. #1716). Linear range of PCR reaction for all primers as well as optimal ratio of 18S primers to competitors to achieve the same level of amplification as the genes of interest was determined.

Primers were obtained from IDT based on the recently published design (Wright et al., *J. Appl. Phys.* 1997; 83:1389), with the following sequence:

```
5'GAAGGCCAAGAAGGCCATC3'    (SEQ ID NO: 1).
```

To design a perfect match of upstream primers for the neonatal sequence, slight modifications of the above common primer was necessary (Table 1). The optimal annealing temperature of these degenerate common primers was, however, unchanged, and they were used in the same manner as the common primer as 5'-oligonucleotides for PCR reactions. The 3'-oligonucleotides used in the PCR reactions were designed from the 3'-untranslated regions of each of the different MHC genes, where the sequences are highly specific for each MHC gene [Wright et al 1997]:

TABLE 1

Oligonucleotide primers used for PCR amplification reactions

| MHC subtype | Common Primer | Antisense Primer |
|---|---|---|
| IIb | 5'GAAGGCCAAGAAGGCCATC3' (SEQ ID NO: 1) | 5'GTGTGATTTCTTCTGTCACC3' (SEQ ID NO: 2) |
| IIx | 5'GAAGGCCAAGAAGGCCATC3' (SEQ ID NO: 1) | 5'GGTCACTTTCCTGCTTTGGA3' (SEQ ID NO: 3) |
| neonatal | 5'GAAGGCCAAGAAGGCCATC3' (SEQ ID NO: 1) | 5'GCGGCCTCCTCAAGATGCGT3' (SEQ ID NO: 4) |

5 units of Taq DNA polymerase (Roche, cat#1146165), 200 μM of each dNTP (Invitrogen, cat. #R725-01), 0.2 μM each MHC primer (IDT), 1 μl of cDNA from reverse transcription reaction and 4 μl of 18S primers: competitors mixture were used in 50 μl PCR reaction. Amplification was carried out in PTC-100 Programmable Thermal Controller (MJ Research, Inc.) with an initial denaturation step of 3 min at 94° C., followed by optimized number of cycles for the MHC primer pair, with each cycle consisting of 45 sec at 94° C., 60 sec at 48° C., 90 sec 72° C., and a final step of 5 min at 72° C. PCR products were analyzed by agarose gel electrophoresis [20-μl aliquots of a 50-μl PCR reaction loaded on a 1.5% agarose gel (in 1x Tris-Acetate-EDTA buffer) containing 0.2 μg/ml ethidium bromide] to visualize the PCR products. Gels were photographed under ultraviolet (UV) light using Polaroid instant film number 57 to generate an image of the gel. Pictures were scanned and the volume of the optical density (OD) of a DNA band was determined by the Image Quant software (Molecular Dynamics), and the background was subtracted (so local background was directly proportional to the amount of DNA over a wide range). Intensity (volume of the OD) of the MHC band was divided by the intensity of the control fragment, thereby correcting for any differences in the efficiency of the PCR reactions. The content of each experimental group MHC gene was calculated as a percentage of the MHC value in the control group (Table 2).

Figure 1B:
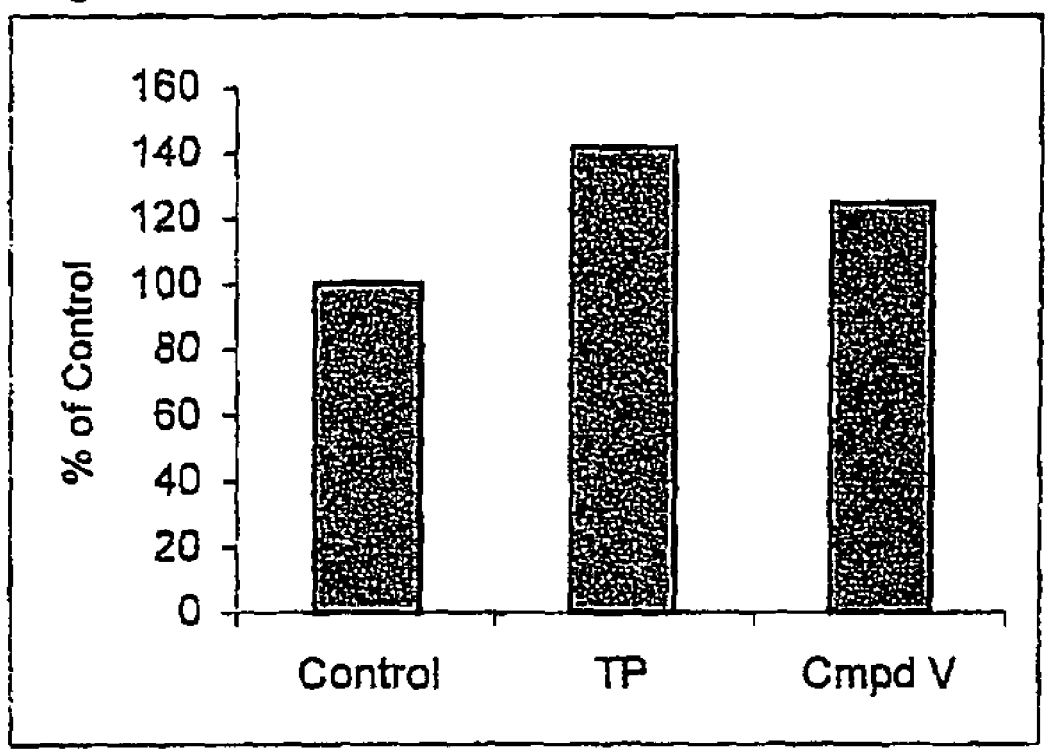

Results:

The masseter muscle dissected from untreated intact female rats was set as the control level (representing 100%) of MHC IIb expression (see histogram in FIG. 1a). Intact female rats treated with androgens were evaluated against the untreated controls for the effect of treatment on MHC IIb from masseter. The results indicate that testosterone propionate has a positive effect on masseter muscle where it increased transcription of MCH type IIb to 142% of untreated control (FIG. 1b). Compound V was found to have a similar effect where it increased level of MHC IIb transcript to 124% (FIG. 1b). Actual untransformed data (PCR results) is shown in FIG. 1a.

In these same rats, the levator ani was dissected and evaluated for the expression pattern of MHC family members. The data indicate that all animals treated with androgens (TP or Compound V) for a period of 14- and 28-days had a muscle present in the location expected for the levator ani, and further characterization of this tissue by RT-PCR demonstrates presence of MHC type IIb and very little expression of MHC subtypes IIx and the neonatal isoform. The SDS-PAGE as well as immunoblotting with a MHC type II specific antibody revealed a single band of apparent molecular weight of about 200 kDa. These results are consistent with the presence of a levator ani muscle [Talmadge R. J. and Roy R. R. *J. Appl. Physiol.* 75(5): 2337-2340, 1993].

TABLE 2

Intensity of the bands resolved on agarose gel expressed as average intensity of all pixels in the spot.

| Treatment | 18 S | II b | II b/18 S | % |
|---|---|---|---|---|
| Control | 102 | 46 | 0.45 | 100 |
| TP | 141 | 90 | 0.64 | 141.5 |
| Compound V | 171 | 96 | 0.56 | 124.5 |

Figure 2:
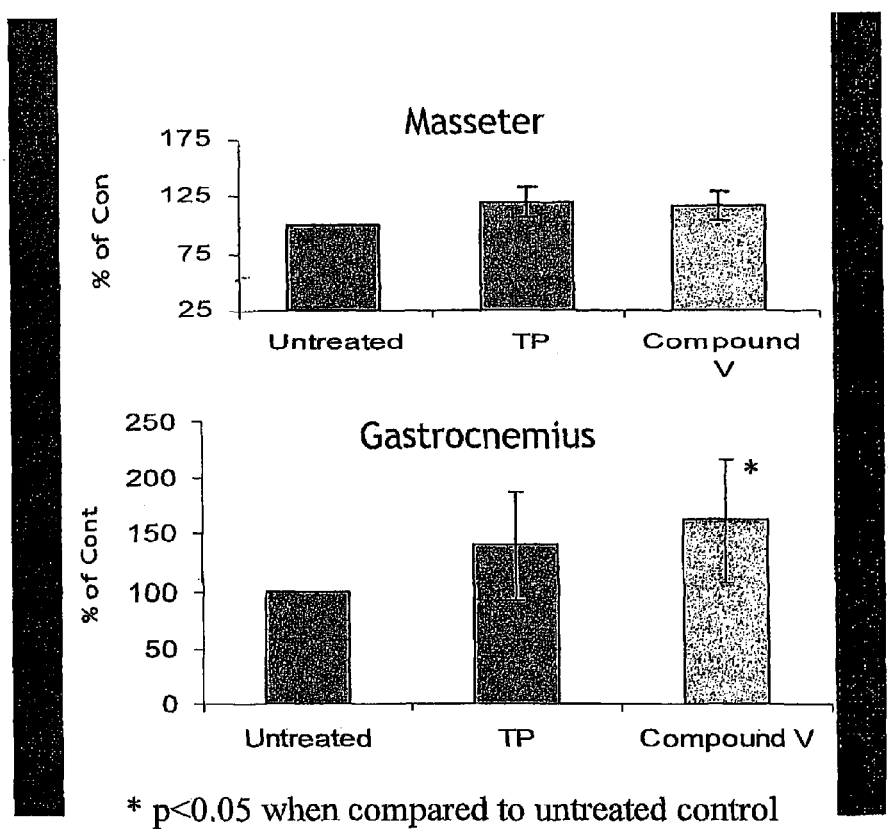
FIG. 2: Effect of testosterone proprionate and Compound V on mysoin heavy chain (MHC) IIb mRNA expression. Intact male Sprague-Dawley rats were treated with placebo, testosterone propionate (5 mg/kg/day), or Compound V (1 mg/kg/day). Histograms showing effect of Compound V on MHC IIb mRNA expression in Masseter muscle (Top) and Gastrocnemius muscle (Bottom).

In a similar experiment with masseter muscle and gastrocnemius muscle, the masseter and gastrocnemius muscles dissected from untreated intact male rats were set as the control level (representing 100%) of MHC IIb expression (FIG. 2). Intact male rats treated with androgens were evaluated against the untreated controls for the effect of treatment on MHC IIb from masseter or gastrocnemius. The results indicate that testosterone propionate has a positive effect on masseter muscle where it increased transcription of MHC type IIb to 120(±14)% of untreated control (FIG. 2—Top). Compound V was also anabolic in muscle, with an increase in MHC type IIb to 117(±13)% (FIG. 2—Top). In gastrocnemius muscle, similar results were observed. Testosterone propionate has a positive effect on gastrocnemius muscle where it increased transcription of MHC type IIb to 139(±47)% of untreated control (FIG. 2—Bottom). Compound V was also anabolic in muscle, with an increase in MHC type IIb to 162(±54)% (FIG. 2—Bottom).

Conclusions:

These results demonstrate that both the selective androgen receptor modulator (SARM) as exemplified by compound V and TP have direct anabolic effects on the musculoskeletal system in intact female and male rats as measured by a net increase in the expression of mRNA for MHC. Additionally, treatment with these anabolic agents for a period of 14- and 28-days resulted in muscular hypertrophy of the levator ani. Testosterone has been recognized as an anabolic androgen for several decades. It has been demonstrated herein, that the selective androgen receptor modulator (SARM) as exemplified by Compound V is an orally bioavailable nonsteroidal agent with tissue selective anabolic effects in male rats and which increases muscle mass. The selective androgen receptor modulator (SARM) as described hereinabove, can be used to treat among other diseases or conditions' catabolic syndromes of sarcopenia associated with aging or chronic illness, and sexual dysfunction in females.

Example 2

Pharmacologic Activity and Tissue-Selectivity of Compounds V and VI in Rats of Varying Hormonal Status Compound V is a potent and efficacious selective androgen receptor modulator (SARM) in castrated male rats. To provide a representative model of the vast majority of men that will eventually receive this drug, Applicants completed a preclinical study to compare the pharmacologic effects and tissue-selectivity of Compound V, Compound VI—another potent SARM, and testosterone propionate (TP) in male rats of varying hormonal status. Male rats with normal testicular function (i.e., intact with no surgical manipulation) were included to examine the effects of Compound V on animals with normal blood levels of testosterone. Male rats that received unilateral orchidectomy (i.e., surgical removal of one testis) were included to examine the effects of Compound V on animals with slight androgen depletion. Male rats that received bilateral orchidectomy (i.e., surgical removal of both testes) were included to examine the effects of Compounds V and VI on androgen-deficient animals.

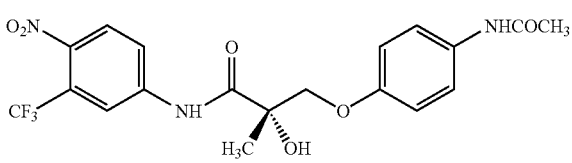

V

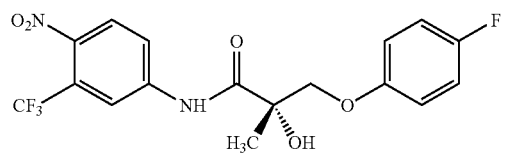

VI

Methods:

Compounds V and VI were synthesized and characterized in the laboratory of Dr. Duane Miller at the University of Tennessee, Memphis, Tenn. Male Sprague-Dawley rats were purchased from Harlan Biosciences (Indianapolis, Ind.). The animals were maintained on a 12-h cycle of light and dark with food and water available ad libitum. All animal studies were reviewed and approved by the Animal Care and Use Committee of The Ohio State University, and conformed to the Principles of Laboratory Animal Care (NIH publication #85-23, revised 1985). Immature male Sprague-Dawley rats weighing 187 to 214 g were randomly distributed into 9 groups of 5 animals. One day before the initiation of drug treatment, groups 4 through 6 and groups 7 through 9 received unilateral or bilateral orchidectomy, respectively, via a midline scrotal incision. Groups 1 through 3 did not undergo surgery. All drugs given to animals were freshly prepared as solutions in polyethylene glycol 300 (PEG 300). Groups 4 and 7 received treatment with vehicle alone (i.e., PEG 300). Animals in groups 3, 6, and 9 received testosterone propionate (TP, 0.5 mg/day) via implantation of subdermal osmotic pumps (Model 2002, Durect Corporation, Palo Alto, Calif.). Animals in groups 2, 5, and 8 received Compound V or Compound VI (0.5 mg/day) via implantation of subdermal osmotic pumps. After 14 days of drug treatment, rats were weighed, anesthetized, and sacrificed. The ventral prostates, seminal vesicles, and levator ani muscle were removed and weighed. Osmotic pumps were also removed from animals to check for correct pump operation. The weights of all organs were normalized to body weight, and analyzed for any statistically significant differences between groups using single-factor ANOVA with the alpha value set a priori at $p<0.05$. The weights of prostates and seminal vesicles were used as indices for evaluation of androgenic activity, and the levator ani muscle weight was used to evaluate the anabolic activity. Statistical analyses of parameters from complete blood count or serum chemical profiling, wherever applicable, were performed by single-factor ANOVA with the alpha value set a priori at $p<0.05$.

Figure 6:
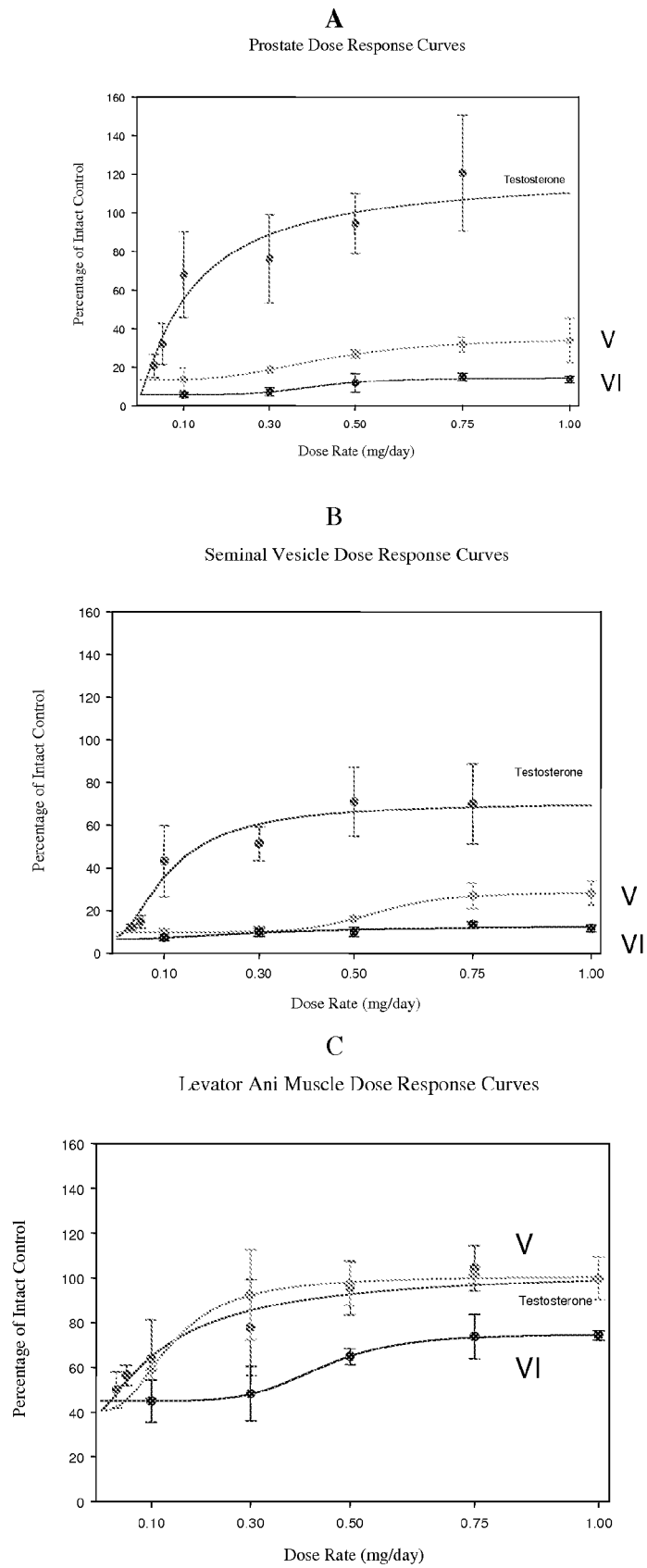
FIG. 6: Dose response curves. Rats were left untreated, or treated with 0.1, 0.3, 0.5, 0.75 and 1.0 mg/day Compound V, Compound VI or testosterone propionate (TP), and the weight of androgen-responsive tissues (prostate—FIG. 6A, semimal vesicles—FIG. 6B and levator ani muscle—FIG. 6C) was determined. The results are plotted as percentage of the intact control.

Results:

As shown in Table 3 and FIG. 3, in intact animals, Compound V decreased the size of the prostate to 79% and, of that observed in control animals (FIG. 3A), with no statistically significant changes in the size of the seminal vesicles (FIG. 3B) or levator ani muscle (FIG. 3C). The pharmacologic effects and tissue selectivity of Compound V were more obvious in hemi-orchidectomized animals (Table 3 and FIG. 4). Compound V decreased the size of the prostate (FIG. 4A) and seminal vesicles (FIG. 4B) to 75% and 79%, respectively, and increased the size of the levator ani muscle (FIG. 4C) to 108% of that observed in untreated hemi-orchidectomized animals. These observations demonstrate that Compound V acts as a partial agonist in prostate and seminal vesicles and as a full agonist in levator ani muscle. No adverse pharmacologic effects were observed. Similarly, as shown in Table 3 and in FIGS. 5 and 6, in castrated animals.

TABLE 3

Comparison of androgenic and anabolic effects of
Compound V and TP on intact, hemi-orchidectomized and castrated
rats (% of intact control, n = 5).

| Organs | | Control | Compound V (0.5 mg/day) | TP (0.5 mg/day) |
|---|---|---|---|---|
| Prostate | Intact | 100.00 ± 13.13 | 79.41 ± 9.32*† | 97.45 ± 10.82 |
| | Hemi- | 86.42 ± 19.52 | 74.69 ± 8.44*† | 98.57 ± 7.98 |
| | Castrated | 7.19 ± 1.25 | 32.55 ± 11.65*†‡ | 76.78 ± 10.43*‡ |
| Seminal | Intact | 100.00 ± 18.84 | 90.54 ± 12.10 | 103.95 ± 13.23 |
| Vesicle | Hemi- | 102.93 ± 7.47 | 78.55 ± 13.58†‡ | 114.19 ± 23.81 |
| | Castrated | 8.97 ± 1.23 | 16.47 ± 5.21*†‡ | 63.48 ± 17.05*‡ |
| Levator Ani | Intact | 100.00 ± 12.69 | 109.15 ± 14.68 | 95.61 ± 9.34 |
| | Hemi- | 92.94 ± 7.83 | 108.10 ± 8.92‡ | 98.63 ± 10.47 |
| | Castrated | 42.74 ± 5.22 | 100.65 ± 10.86‡ | 87.27 ± 10.25‡ |

*$p < 0.05$ compared to intact control group.
†$p < 0.05$ compared to TP of same surgical status (i.e., intact, hemi-orchidectomized, or castrate).
‡$p < 0.05$ compared to control group of same surgical status.

A comparison of the androgenic and anabolic activities of Compound V and Compound VI is provided in Table 4.

TABLE 4

Table 2. Comparison of Androgenic and Anabolic Activities of Compound VI and Compound V to TP

| | Organs | Treatment | $E_{max}$ (% of Intact Control) | Relative Afficacy | $ED_{50}$ (mg/day) | Relative Potency |
|---|---|---|---|---|---|---|
| Androgenic | Prostate | TP | 120.6 ± 13.4 | 1.00 | 0.13 ± 0.03 | 1.00 |
| | | Cmpd VI | 14.5 ± 0.7 | 0.12 | 0.42 ± 0.04 | 0.31 |
| | | Cmpd V | 35.2 ± 0.4 | 0.29 | 0.43 ± 0.01 | 0.30 |
| | Seminal | TP | 70.0 ± 18.8 | 1.00 | 0.12 ± 0.02 | 1.00 |
| | Vesicle | Cmpd VI | 12.7 ± 3.1 | 0.18 | 0.38 ± 0.26 | 0.32 |
| | | Cmpd V | 28.5 ± 0.8 | 0.40 | 0.55 ± 0.02 | 0.22 |
| Anabolic | Levator | TP | 104.2 ± 10.1 | 1.00 | 0.15 ± 0.03 | 1.00 |
| | Ani | Cmpd VI | 74.9 ± 0.4 | 0.72 | 0.44 ± 0.01 | 0.34 |
| | Muscle | Cmpd V | 101.0 ± 1.0 | 0.97 | 0.14 ± 0.01 | 1.07 |

Conclusions:

Compound V demonstrated potent and tissue-selective pharmacologic effects in intact, hemi-orchidectomized and castrated male rats. Compound V led to significant decreases in prostate weights in intact and hemi-orchidectomized animals, and was less effective than TP at increasing the weight of the prostate in castrated animals. Similar pharmacologic effects were noted in the seminal vesicles (another organ generally considered as a marker of androgenic effects), with the exception that Compound V had no effect on the weight of the seminal vesicles in intact animals. Compound V treatment led to significant increases in the weight of the levator ani muscle in hemi-orchidectomized and castrated animals. These effects were greater than those observed with TP. These data demonstrate the tissue-selective pharmacologic effects of Compound V. It is important to note that these effects were observed in the absence of any significant changes in plasma concentrations of FSH, LH and testosterone (not shown). In summary, these data show that Compound V elicits an optimal pharmacological profile in male animals, identifying it as the first member of a new class of orally bioavailable and tissue-selective SARMs.

Example 3

Pharmacologic Activity and Tissue-Selectivity of Selected Halogenated Selective Androgen Receptor Modulators in Rats Compounds VI-X in Table 5 were synthesized and characterized in the laboratory of Dr. Duane Miller at the University of Tennessee, Memphis, Tenn.

The tissue-selectivity and pharmacologic effects of Compounds VI-X were determined as described above in Example 2.

Table 5 shows the chemical structures and binding affinities of Compounds VI-IX. Binding affinities were determined as described in He et al. *Eur. J. Med. Chem.* (2002), 619-634; and as described in Mukherjee et al. *Xenobiotica* (1996), 26, 117-122.

TABLE 5

| Compound Name | Structure | Molecular weight | RBA % | Ki (nM) |
|---|---|---|---|---|
| VI | O₂N-, F₃C- phenyl-NH-C(O)-C(CH₃)(OH)-CH₂-O-phenyl-F | 402 | 26.4 | 2.3 ± 0.06 |
| VII | O₂N-, F₃C- phenyl-NH-C(O)-C(CH₃)(OH)-CH₂-O-phenyl-Cl | 419 | 7.6 | 8.6 ± 1.2 |
| VIII | O₂N-, F₃C- phenyl-NH-C(O)-C(CH₃)(OH)-CH₂-O-phenyl-Br | 462 | 5.3 | 12.6 ± 1.8 |
| IX | O₂N-, F₃C- phenyl-NH-C(O)-C(CH₃)(OH)-CH₂-O-phenyl-I | 510 | 2.7 | 23 ± 1.6 |

Results:

As shown in FIG. 7, Compounds VI-IX demonstrated tissue-selective pharmacological effects in castrated male rats, with higher efficacy in anabolic tissues (i.e. levator ani) as compared to androgenic tissues (i.e. prostate and seminal vesicles). Compounds VI-IX all had an anabolic effect, increasing the weight of the levator ani muscle in a dose-dependent manner. Compounds VI, VIII and IX (FIGS. 7A, C and D, respectively) increased the weight of the levator ani muscle to values close to those of the intact controls. The effect of compound VII (FIG. 7B) was even more pronounced—increasing the weight of the levator ani muscle to values exceeding those of intact controls. There were no statistically significant changes in the sizes of the prostate or seminal vesicles. These data demonstrate the tissue-selective pharmacologic effects of Compounds VI-IX.

Example 4

Pharmacologic Activity and Tissue-Selectivity of Compound X in Rats

Compound X (Table 6) was synthesized and characterized in the laboratory of Dr. Duane Miller at the University of Tennessee, Memphis, Tenn.

The tissue-selectivity and pharmacologic effects of Compound X were determined as above in Examples 2 and 3.

Table 6 shows the chemical structure and binding affinity of

Compound X. Binding affinities were determined as described in He et al.

TABLE 6

| Compound Name | Structure | Molecular weight | Ki (nM) |
|---|---|---|---|
| X | [Structure: 4-cyano-3-(trifluoromethyl)phenyl-NH-C(=O)-C(CH3)(OH)-CH2-O-C6H4-F] | 382.3 | 3.3 ± 0.08 |

Figure 8:
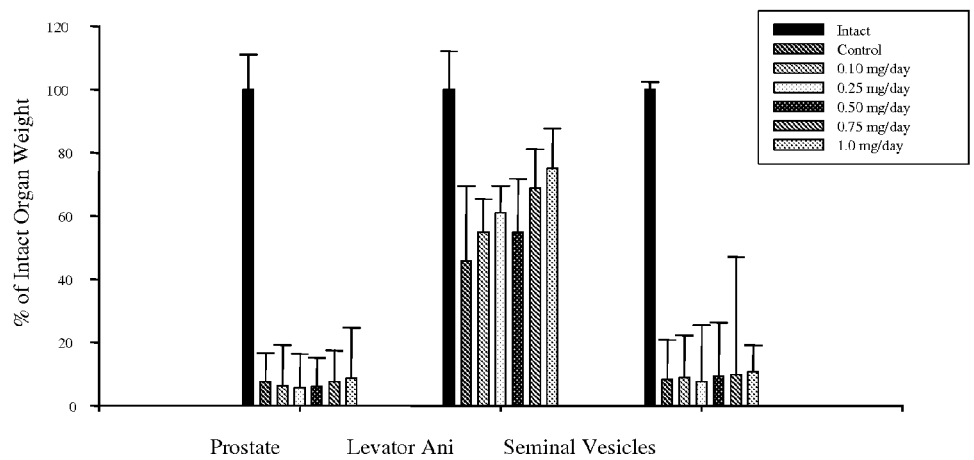
FIG. 8: Dose response curves of Compound X in rats. Castrated rats were left untreated (control), or treated with 0.1, 0.25, 0.5, 0.75 and 1 mg/day of Compound X, and the weights of androgen-responsive tissues (prostate and semimal vesicles) and levator ani muscle were determined. Intact represents male rats with normal testicular function (no surgical manipulation).

Results:

As shown in Table 7 and FIG. 8, Compound X demonstrated tissue-selective pharmacological effects in castrated male rats, with higher efficacy in anabolic tissues (i.e. levator ani) as compared to androgenic tissues (i.e. prostate and seminal vesicles). Compound X demonstrated little pharmacologic activity in the prostate (8.7±1.39% of intact at 1.0 mg/day dose) and seminal vesicles (10.7±0.91% of intact at 1.0 mg/day dose), suggesting that it acts as a weak partial agonist in these tissues. Importantly, Compound X demonstrates highly efficacious anabolic activity at 1.0 mg/day dose, returning the levator ani muscle to 75.2±9.51% of that observed in intact animals.

TABLE 7

| | Average (Mean ± S.D.) Organ Weights | | |
|---|---|---|---|
| | Prostate | Levator Ani | Seminal Vesicles |
| Intact Control | 100 ± 11.28 | 100 ± 12.12 | 100 ± 2.48 |
| Castrated Control | 7.6 ± 0.68 | 45.9 ± 10.84 | 8.4 ± 1.05 |
| 0.10 mg/day | 6.4 ± 0.82 | 54.9 ± 5.77 | 8.8 ± 1.18 |
| 0.25 mg/day | 5.7 ± 0.61 | 61.0 ± 5.23 | 7.6 ± 1.37 |
| 0.50 mg/day | 6.2 ± 0.56 | 55.0 ± 9.23 | 9.3 ± 1.57 |
| 0.75 mg/day | 7.6 ± 0.74 | 68.9 ± 8.46 | 9.8 ± 3.65 |
| 1.00 mg/day | 8.7 ± 1.39 | 75.2 ± 9.51 | 10.7 ± 0.91 |

Example 5

Pharmacologic Activity and Tissue-Selectivity of Compounds XI and XII in Rats

Compounds XI and XII (Table 8) was synthesized and characterized in the laboratory of Dr. Duane Miller at the University of Tennessee, Memphis, Tenn.

The tissue-selectivity and pharmacologic effects of Compounds XI and XII were determined as described above in Examples 2-4.

Table 8 shows the chemical structure and binding affinity of Compounds XI and XII. Binding affinities were determined as described in He et al.

TABLE 8

| Compound Name | Molecular Weight | Structure | Ki (nM) | RBA (%) |
|---|---|---|---|---|
| XI | $C_{17}H_{13}F_5N_2O_5$ 420.29 | [Structure: 4-nitro-3-(trifluoromethyl)phenyl-NH-C(=O)-C(CH3)(OH)-CH2-O-C6H3-3,4-F2] | 3.4 ± 0.56 | 17.6 |
| XII | $C_{17}H_{10}F_8N_2O_5$ 474.26 | [Structure: 4-nitro-3-(trifluoromethyl)phenyl-NH-C(=O)-C(CH3)(OH)-CH2-O-C6F5] | 1.37 ± 0.34 | 13.3 |

Figure 9:
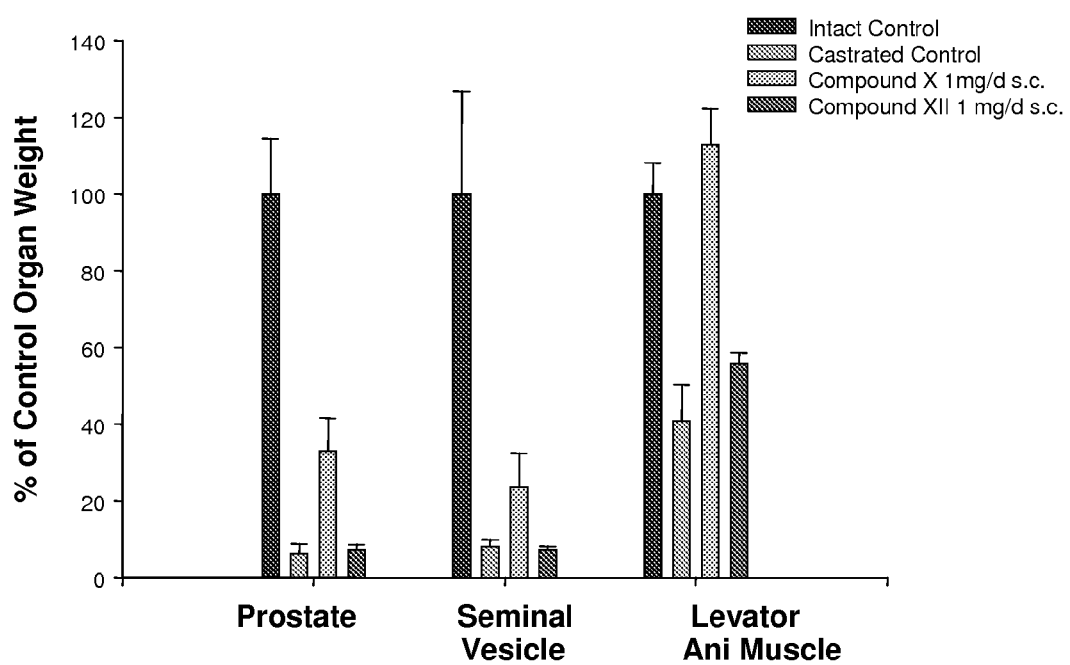
FIG. 9: Androgenic and Anabolic activity of Compounds XI and XII in rats. Male rats received bilateral orchidectomy (Castrated) and were left untreated (Castrated Control), or were treated with 1 mg/day Compound XI or compound XII, and the weights of androgen-responsive tissues (prostate and semimal vesicles) and levator ani muscle were determined. Intact represents male rats with normal testicular function (no surgical manipulation).

Results:

As shown in Table 9 and FIG. 9, Compounds XI and XII demonstrated tissue-selective pharmacological effects in castrated male rats, with higher efficacy in anabolic tissues (i.e. levator ani) as compared to androgenic tissues (i.e. prostate and seminal vesicles). Compound XI demonstrated partial pharmacologic activity in the prostate (33.1±8.5% of intact at 1.0 mg/day dose after injection) and seminal vesicles (23.6±8.8% of intact at 1.0 mg/day dose after injection), suggesting that it acts as a weak partial agonist in these tissues. Importantly, Compound XII demonstrated highly efficacious anabolic activity at 1.0 mg/day dose, returning the levator ani muscle to 112.8±9.4% of that observed in intact animals (daily injection), and 122.5±10.4% of that observed in intact animals (pump). Compound XII demonstrated little pharmacologic activity in the prostate (7.2±1.4% of intact at 1.0 mg/day dose) and seminal vesicles (7.2±0.9% of intact at 1.0 mg/day dose), suggesting that it acts as a weak partial agonist in these tissues. Importantly, Compound XII demonstrated anabolic activity at 1.0 mg/day dose, returning the levator ani muscle to 55.83±2.84% of that observed in intact animals.

TABLE 9

|  | Intact | Castrated | XI* (pump) | XI (daily injection) | XII (daily injection) |
|---|---|---|---|---|---|
| Prostate | 100 ± 14.3 | 6.2 ± 2.5 | 40.3 ± 10.0 | 33.1 ± 8.5 | 7.2 ± 1.4 |
| Seminal Vesicles | 101 ± 26.8 | 8.1 ± 1.8 | 30.9 ± 5.7 | 23.6 ± 8.8 | 7.2 ± 0.9 |
| Levator Ani Muscle | 102 ± 8.1 | 40.9 ± 9.4 | 122.5 ± 10.4 | 112.8 ± 9.4 | 55.83 ± 2.84 |

*Reference group that treated with GTx02-CK2-1 1 mg/day via osmotic pump.

Example 6

Effect of Compound V on Skeletal Muscle Mass and Strength in Castrated Male Rats The effect of Compound V on skeletal muscle mass and strength was examined in a castrated male rat model.

Materials and Methods

Animals: Male, Sprague-Dawley rats (12 weeks old) were ORX at the beginning of the study. A group of sham-operated male rats was also included as intact control. The ORX animals (279-324 g) were randomly distributed into groups of 7 or 8 animals. Animals were maintained for 12 weeks after orchidectomy and were then treated with S-4 (3 or 10 mg/kg), DHT (3 mg/kg), or vehicle for 8 weeks. The intact animals were also treated with vehicle during the treatment period. The dosage was adjusted weekly based on animals' body weights. The drugs were dissolved in DMSO:PEG300 (20:80, v:v) and administered via daily subcutaneous injections. At the end of treatment, animals were weighed, anesthetized, and sacrificed within 8 hours after the last dose. The soleus muscle from the left rear leg was dissected immediately and was used for muscle strength measurements. The androgenic (ventral prostate and seminal vesicle) and anabolic tissues (levator ani muscle), and the soleus muscle from the right rear leg were removed and weighed. Blood samples were collected and used for the measurement of serum markers, including IGF-I and osteocalcin, using commercially available EIA kits. Statistical analyses of all the parameters were performed by single-factor ANOVA with the alpha value set a priori at p<0.05.

Muscle Contractile Force Measurement: The soleus muscle was isolated and then mounted in the experimental chamber. The muscle was perfused in oxygenated (95% $O_2$, 5% $CO_2$) Krebs-Ringer solution at room temperature (20-25° C.). The proximal tendon was attached to a rigid post, and the distal tendon was attached to a Kulite BG1000 transducer (Kulite Semiconductor Products, Inc., Leonia, N.J.) with 4.0 silk. The muscle was stimulated using a Grass S48 Stimulator (Quincy, Mass.) through two platinum field electrodes attached to the chamber walls. The output from the transducer was recorded using ASI Dynamic Muscle Control and Analysis Software from Aurora Scientific Inc. (Aurora, Canada). A force—tension curve was obtained by stimulating the muscle at supermaximal voltage (10 Volts) for 2 ms while stretching the muscle in 1 mm increments. Once the optimal length of the muscle (L0, muscle length at which maximal twitch tension was achieved) was identified, maximal tetanic tension (P0), time to peak twitch tension (tPt), and time to one half relaxation (t½R) were measured at L0.

Peak twitch tension was elicited with supermaximal voltage (10 Volts) as square-wave pulses of 2 ms duration delivered at 0.1 Hz frequency. Sixteen continuous twitches were recorded, and one out of every three twitches was analyzed. The average of five measurements for each parameter was reported for each muscle sample. Tetanus was evoked with 3.0-s trains of stimuli at 2 ms duration and 40 Hz frequency. Three tetani were obtained for each muscle, the average of three measurements of P0 was reported. After the measurements, the soleus muscle was weighed, and the cross sectional area (CSA) of the muscle was estimated using the following equation:

CSA (mm2)=muscle mass (mg)/[muscle optimal length (mm)×muscle density (mg/mm³)]

Muscle density was assumed to be 1 mg/mm³ in rat skeletal muscle. Contractile force measurements were normalized to the CSA of the muscle prior to statistical comparison.

Results

Figure 10:
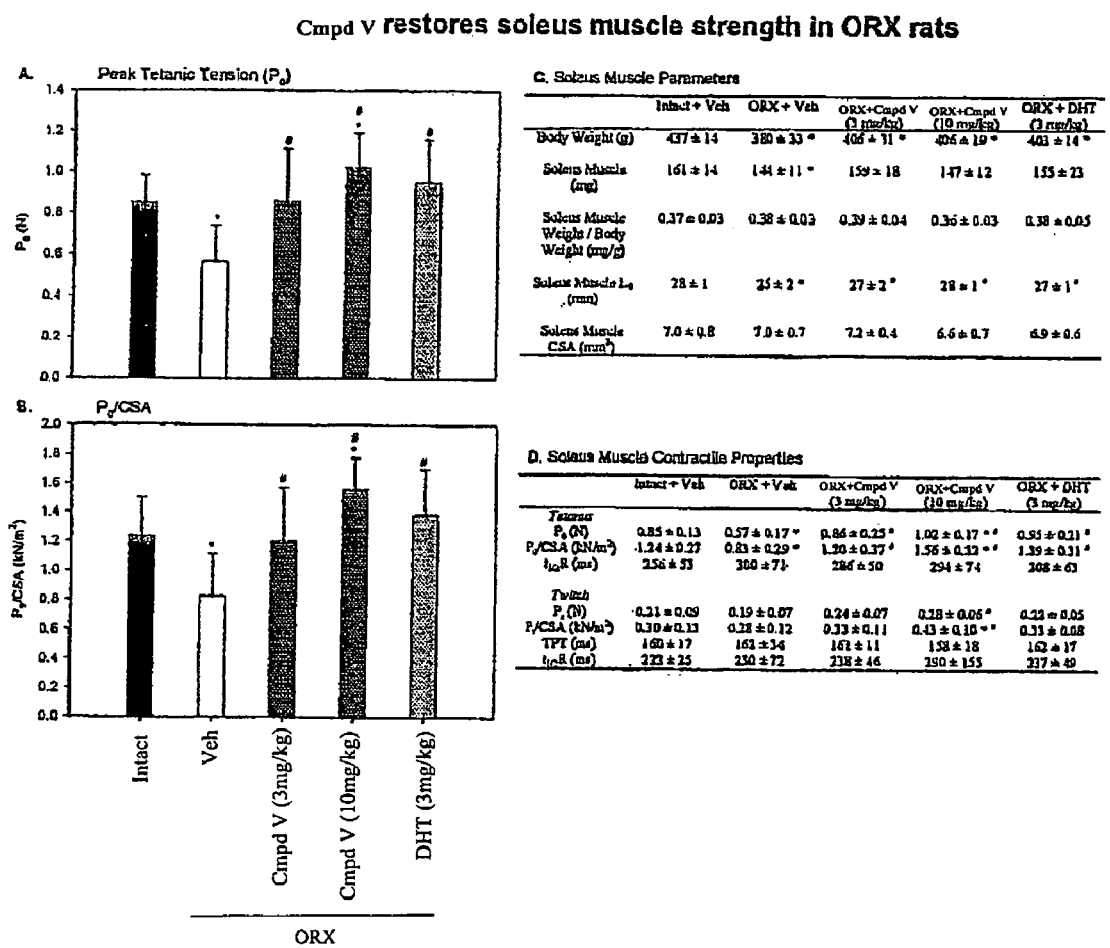
FIG. 10: Effects of Compound V on soleus muscle mass and contractile properties. Twelve weeks after ORX, animals were treated with vehicle, Compound V (3 or 10 mg/kg), or DHT (3 mg/kg) for 8 weeks. Data are presented as mean±SD. A. Peak tetanic tension. B. P0/CSA.

As demonstrated in FIG. 10, Compound V is able to restore soleus muscle strength in ORX rats. Twelve weeks after ORX, animals were treated with vehicle, Compound V (3 or 10 mg/kg), or DHT (3 mg/kg) for 8 weeks. Data are presented as mean±SD. FIG. 10 A shows the peak titanic tension. FIG. 10B shows P0/CSA. As demonstrated, Compound V and DHT treatments restored ORX-caused loss in P0 and P0/CSA. The normalized soleus muscle weights and CSA of the muscle showed no significant difference between treatment groups (Not shown). In addition Compound V and DHT treatments did not cause significant changes in contraction kinetics of twitch or tetanus (not shown).

The data shows that Compound V shows a strong anabolic effect in skeletal muscle. Compound V restored soleus muscle strength without changing normalized muscle mass.

Example 7

Compound V Regulates MHC Isoform Expression in Cardiac Muscle but not in Soleus Muscle in ORX rats Materials and Methods The castrated male rat model used in Example 6 was used for these experiments.

Electrophoretic Separation of Skeletal and Cardiac Myosin Heavy Chain (MHC) Isoforms: Samples of the soleus and left ventricular muscle were homogenized in sample buffer. Dissolved samples were further diluted (1:10/v:v) with sample buffer before loading on the gel. An aliquot (3 μl) of each sample was loaded on each lane of the gel. For soleus muscle sample analysis, the stacking and separating gels (0.75 mm thick) consisted of 4 and 7% acrylamide (wt/vol), respectively, with acrylamide:bis-acrylamide ratio of 50:1. The stacking gel included 5% glycerol, and the separating gel included 30% glycerol. 2-Mercaptoethanol was added to the upper electrode buffer at a final concentration of 10 mM. Gels were run in a Hoefer SE600 unit (Hoefer Scientific, San Francisco, Calif.) at 8° C., with a constant voltage of 330 V for 23 hours. The ventricular sample analyses were conducted in a similar manner, except that the separating gel consisted of 6% acrylamide and 5% glycerol and the gels were run at 200 V for 20 hours. The gels were then fixed and silver-stained. The stained gels were analyzed using a GS 300 scanning densitometer (Hoefer Scientific).

Results

Figure 11:
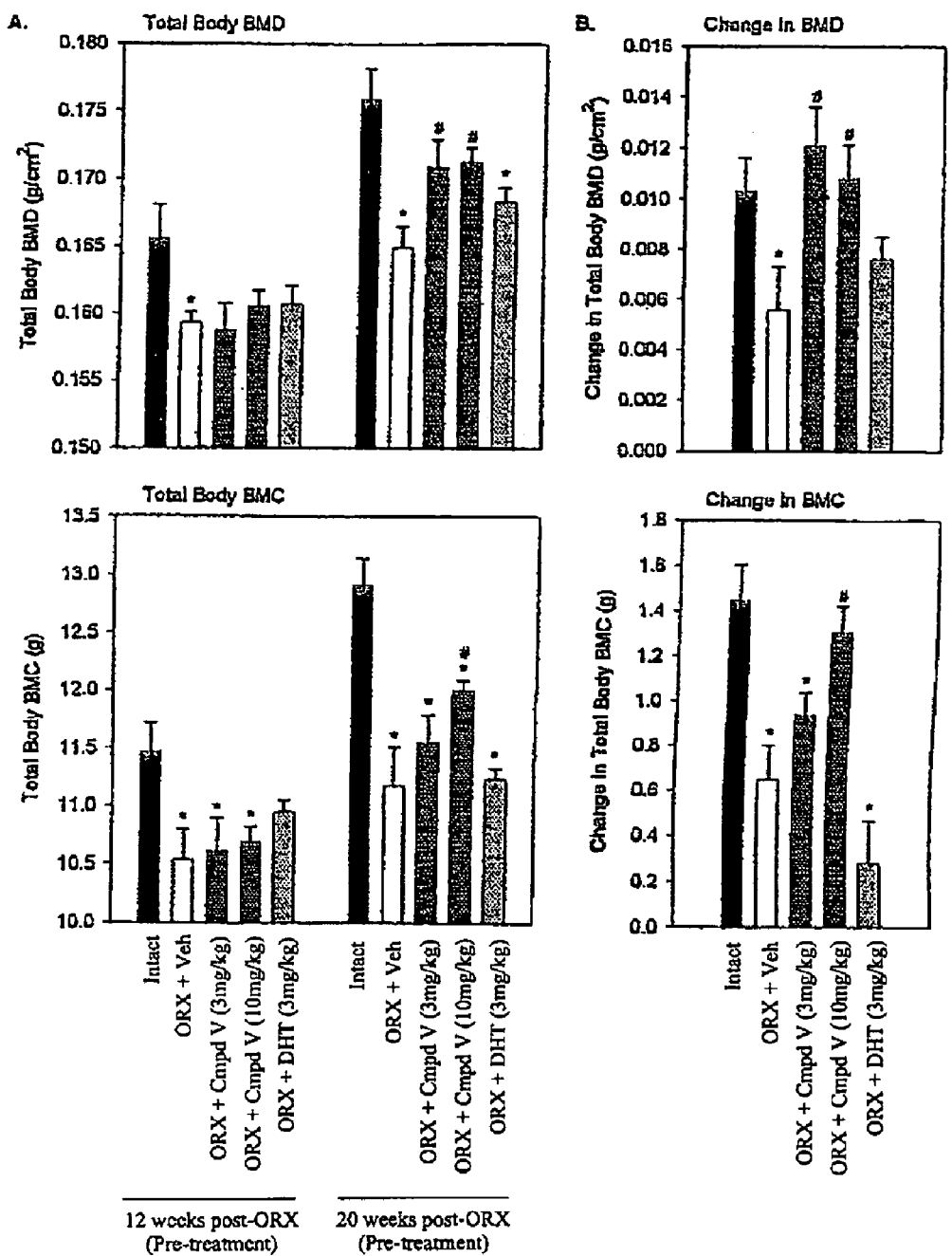
FIG. 11: MHC isoform expression in soleus muscle (A) and cardiac ventricular muscle (B) (n=7-8). Twelve weeks after ORX, animals were treated with vehicle, Compound V (3 or 10 mg/kg), or DHT (3 mg/kg) for 8 weeks. Data are presented as mean±SD.

MHC isoform expression in soleus muscle (A) and cardiac ventricular muscle (B) (n=7-8) is shown in FIGS. 11A and B, respectively. Twelve weeks after ORX, animals were treated with vehicle, Compound V (3 or 10 mg/kg), or DHT (3 mg/kg) for 8 weeks. Data are presented as mean±SD. FIG. 11A shows that Compound V and DHT treatment did not affect MHC isoform expression in soleus muscle in ORX animals. FIG. 11B shows that ORX decreased MHC-α expression in ventricular muscle; Compound V and DHT treatments reversed the change.

Cardiac MHC-α expression was regulated by DHT and Compound V. However, MHC isoform expression in soleus muscle was not regulated by DHT or Compound V, suggesting that the increase in soleus muscle strength was not related to MHC isoform expression.

In summary, these data demonstrate that Compound V has great therapeutic potential in male hormone replacement therapy and the treatment of disease-related muscle wasting and osteoporosis.

It will be appreciated by a person skilled in the art that the present invention is not limited by what has been particularly shown and described hereinabove. Rather, the scope of the invention is defined by the claims which follow:

---

What is claimed is:

1. A method of treating a subject suffering from a muscle wasting disorder, comprising the step of administering to said subject a selective androgen receptor modulator (SARM) compound represented by the structure of formula VI:

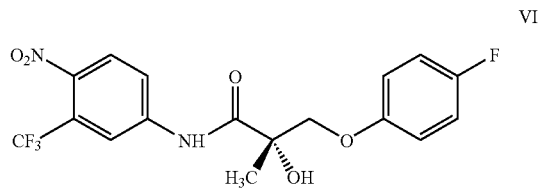

or formula X:

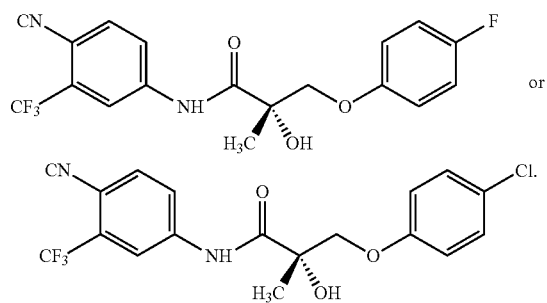

2. The method according to claim 1, wherein said SARM compound is represented by the following structure:

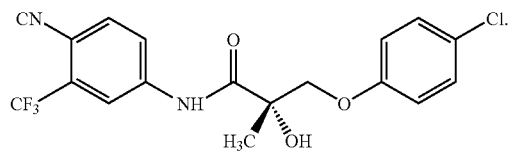

3. The method according to claim 1, wherein said SARM compound is represented by the structure of formula X:

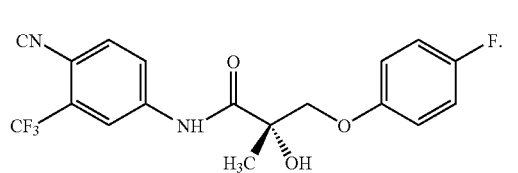

4. The method according to claim 1, comprising administering an isomer, pharmaceutically acceptable salt, pharmaceutical product, or N-oxide, of said SARM compound, or any combination thereof.

5. The method according to claim 1, wherein said muscle wasting disorder is due to a pathology, illness, disease or condition.

6. The method according to claim 5, wherein said pathology, illness, disease or condition is neurological, infectious, chronic or genetic.

7. The method according to claim 5, wherein said pathology, illness, disease or condition is a muscular dystrophy, a muscular atrophy, X-linked spinal-bulbar muscular atrophy (SBMA) or a cachexia.

8. The method according to claim 1, wherein said muscle wasting disorder is an age-associated muscle wasting disorder or a disuse deconditioning-associated muscle wasting disorder.

9. The method according to claim 1, wherein said muscle wasting disorder is a chronic muscle wasting disorder.

10. The method according to claim 1, wherein said administering comprises administering a pharmaceutical composition comprising said SARM and/or its isomer, pharmaceutically acceptable salt, pharmaceutically product, N-oxide, or any combination thereof; and a pharmaceutically acceptable carrier.

11. The method according to claim 10, wherein said administering comprises intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

12. The method according to claim 10, wherein said pharmaceutical composition is a pellet, a tablet, a capsule, a solution, a suspension, an emulsion, an elixir, a gel, a cream, a suppository or a parenteral formulation.

13. A method of treating or reducing muscle loss in a subject suffering from a muscle wasting disorder, comprising the step of administering to said subject a selective androgen receptor modulator (SARM) compound represented by the following structure of formula VI:

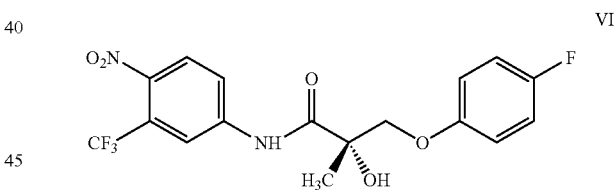

or formula X:

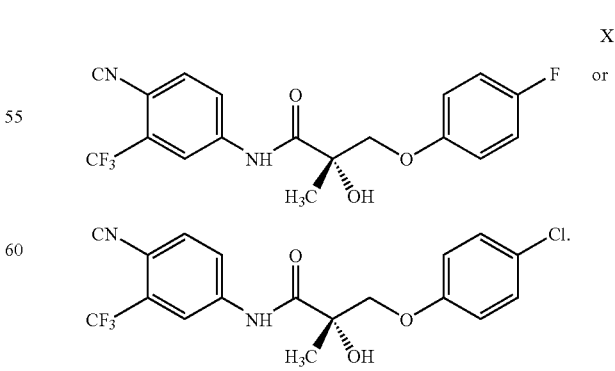

14. The method according to claim 13, wherein said SARM compound is represented by the following structure:

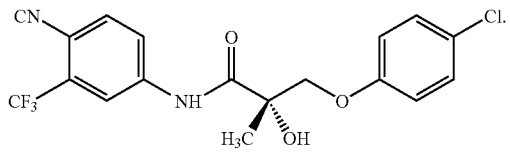

15. The method according to claim 13, wherein said SARM compound is represented by the structure of formula X:

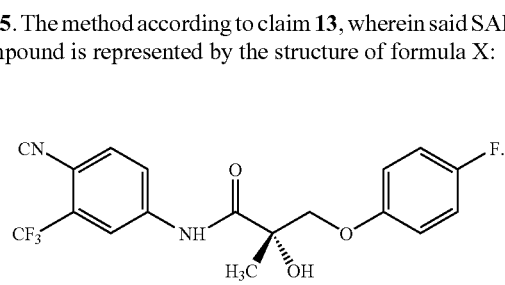

16. The method according to claim 13, comprising administering an isomer, pharmaceutically acceptable salt, pharmaceutical product, or N-oxide, of said SARM compound, or any combination thereof.

17. The method according to claim 13, wherein said muscle wasting disorder is due to a pathology, illness, disease or condition.

18. The method according to claim 17, wherein said pathology, illness, disease or condition is neurological, infectious, chronic or genetic.

19. The method according to claim 17, wherein said pathology, illness, disease or condition is a muscular dystrophy, a muscular atrophy, X-linked spinal-bulbar muscular atrophy (SBMA) or a cachexia.

20. The method according to claim 13, wherein said muscle wasting disorder is an age-associated muscle wasting disorder or a disuse deconditioning-associated muscle wasting disorder.

21. The method according to claim 13, wherein said muscle wasting disorder is a chronic muscle wasting disorder.

22. The method according to claim 13, wherein said administering comprises administering a pharmaceutical composition comprising said SARM and/or its isomer, pharmaceutically acceptable salt, pharmaceutically product, N-oxide, or any combination thereof; and a pharmaceutically acceptable carrier.

23. The method according to claim 22, wherein said administering comprises intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

24. The method according to claim 22, wherein said pharmaceutical composition is a pellet, a tablet, a capsule, a solution, a suspension, an emulsion, an elixir, a gel, a cream, a suppository or a parenteral formulation.

25. A method of treating or reducing muscle wasting in a subject suffering from a muscle wasting disorder, comprising the step of administering to said subject a selective androgen receptor modulator (SARM) compound represented by the structure of formula VI:

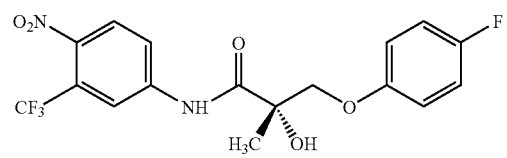

or formula X:

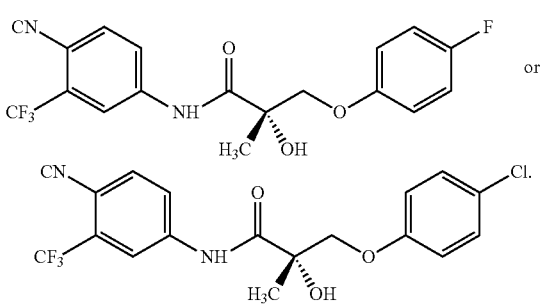

26. The method according to claim 25, wherein said SARM compound is represented by the following structure:

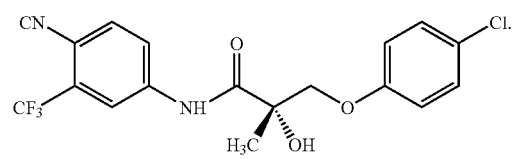

27. The method according to claim 25, wherein said SARM compound is represented by the structure of formula X:

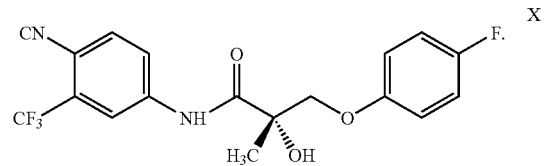

28. The method according to claim 25, comprising administering an isomer, pharmaceutically acceptable salt, pharmaceutical product, or N-oxide, of said SARM compound, or any combination thereof.

29. The method according to claim 25, wherein said muscle wasting disorder is due to a pathology, illness, disease or condition.

30. The method according to claim 29, wherein said pathology, illness, disease or condition is neurological, infectious, chronic or genetic.

31. The method according to claim 29, wherein said pathology, illness, disease or condition is muscular dystrophy, a muscular atrophy, X-linked spinal-bulbar muscular atrophy (SBMA) or a cachexia.

32. The method according to claim 25, wherein said muscle wasting disorder is an age-associated muscle wasting disorder or a disuse deconditioning-associated muscle wasting disorder.

33. The method according to claim 25, wherein said muscle wasting disorder is a chronic muscle wasting disorder.

34. The method according to claim 25, wherein said administering comprises administering a pharmaceutical composition comprising said SARM and/or its isomer, pharmaceutically acceptable salt, pharmaceutically product, N-oxide, or any combination thereof; and a pharmaceutically acceptable carrier.

35. The method according to claim 34, wherein said administering comprises intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

36. The method according to claim 34, wherein said pharmaceutical composition is a pellet, a tablet, a capsule, a solution, a suspension, an emulsion, an elixir, a gel, a cream, a suppository or a parenteral formulation.

37. A method of treating or reducing muscle protein catabolism in a subject suffering from a muscle wasting disorder, comprising the step of administering to said subject a selective androgen receptor modulator (SARM) compound represented by the structure of formula VI:

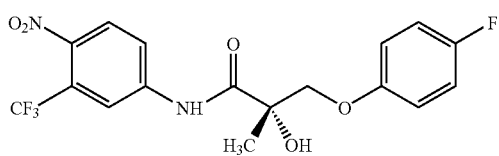

VI or formula X:

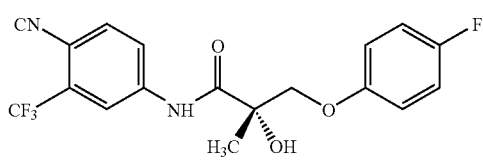

X or

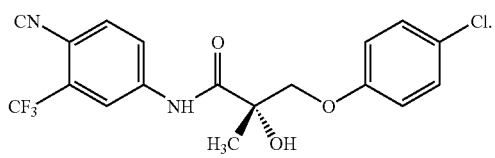

38. The method according to claim 37, wherein said SARM compound is represented by the following structure:

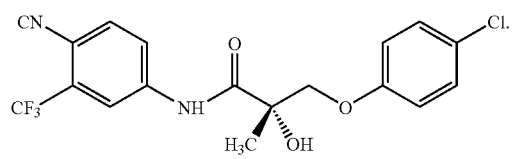

39. The method according to claim 37, wherein said SARM compound is represented by the structure of formula X:

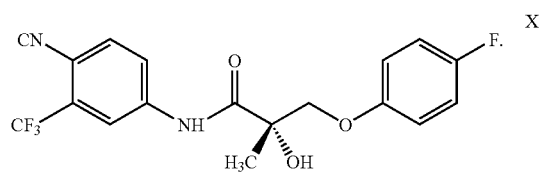

X

40. The method according to claim 37, comprising administering an isomer, pharmaceutically acceptable salt, pharmaceutical product, or N-oxide, of said SARM compound, or any combination thereof.

41. The method according to claim 37, wherein said muscle wasting disorder is due to a pathology, illness, disease or condition.

42. The method according to claim 41, wherein said pathology, illness, disease or condition is neurological, infectious, chronic or genetic.

43. The method according to claim 41, wherein said pathology, illness, disease or condition is muscular dystrophy, a muscular atrophy, X-linked spinal-bulbar muscular atrophy (SBMA) or a cachexia.

44. The method according to claim 37, wherein said muscle wasting disorder is an age-associated muscle wasting disorder or a disuse deconditioning-associated muscle wasting disorder.

45. The method according to claim 37, wherein said muscle wasting disorder is a chronic muscle wasting disorder.

46. The method according to claim 37, wherein said administering comprises administering a pharmaceutical composition comprising said SARM and/or its isomer, pharmaceutically acceptable salt, pharmaceutically product, N-oxide, or any combination thereof; and a pharmaceutically acceptable carrier.

47. The method according to claim 46, wherein said administering comprises intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

48. The method according to claim 46, wherein said pharmaceutical composition is a pellet, a tablet, a capsule, a solution, a suspension, an emulsion, an elixir, a gel, a cream, a suppository or a parenteral formulation.

* * * * *